(12) United States Patent
Ali

(10) Patent No.: US 12,575,944 B2
(45) Date of Patent: Mar. 17, 2026

(54) INTERBODY FUSION DEVICES, SYSTEMS AND METHODS

(71) Applicant: RAED M. ALI, M.D., INC., Newport Coast, CA (US)

(72) Inventor: Raed Ali, Newport Coast, CA (US)

(73) Assignee: Raed M. Ali, M.D., Inc., Newport Coast, CA (US)

( * ) Notice: Subject to any disclaimer, the term of this patent is extended or adjusted under 35 U.S.C. 154(b) by 354 days.

(21) Appl. No.: 17/722,220

(22) Filed: Apr. 15, 2022

(65) Prior Publication Data

US 2022/0346972 A1 Nov. 3, 2022

Related U.S. Application Data

(63) Continuation of application No. 16/779,289, filed on Jan. 31, 2020, now Pat. No. 11,304,824, which is a
(Continued)

(51) Int. Cl.
*A61F 2/46* (2006.01)
*A61F 2/44* (2006.01)
(Continued)

(52) U.S. Cl.
CPC ............ *A61F 2/4611* (2013.01); *A61F 2/442* (2013.01); *A61F 2/4455* (2013.01); *A61F 2/447* (2013.01);
(Continued)

(58) Field of Classification Search
CPC ..................................................... A61F 2/4611
See application file for complete search history.

(56) References Cited

U.S. PATENT DOCUMENTS 4,653,481 A 3/1987 Howland et al.
4,790,303 A 12/1988 Steffee
(Continued)

FOREIGN PATENT DOCUMENTS

EP 2 229 902 3/2010
KR 10-2007-0104337 10/2007
(Continued)

OTHER PUBLICATIONS

International Search Report and Written Opinion for Application No. PCT/US2014/025035 (the PCT counterpart of this application) dated Jul. 18, 2014.
(Continued)

*Primary Examiner* — Christian A Sevilla
(74) *Attorney, Agent, or Firm* — Knobbe, Martens, Olson & Bear, LLP

(57) ABSTRACT

According to some embodiments, a method of inserting a lateral implant within an intervertebral space defined between an upper vertebral member and a lower vertebral member includes creating a lateral passage through a subject in order to provide minimally invasive access to the intervertebral space, at least partially clearing out native tissue of the subject within and/or near the intervertebral space, positioning a base plate within the intervertebral space, wherein the base plate comprise an upper base plate and a lower base plate and advancing an implant between the upper base plate and the lower base plate so that the implant is urged into the intervertebral space and the upper vertebral member is distracted relative to the lower vertebral member.

7 Claims, 17 Drawing Sheets

Related U.S. Application Data continuation of application No. 15/865,154, filed on Jan. 8, 2018, now Pat. No. 10,548,742, which is a continuation of application No. 14/774,640, filed as application No. PCT/US2014/025035 on Mar. 12, 2014, now Pat. No. 9,861,495.

(60) Provisional application No. 61/786,160, filed on Mar. 14, 2013.

(51) Int. Cl.
| | |
|---|---|
| *A61F 2/30* | (2006.01) |
| *A61F 2/48* | (2006.01) |

(52) U.S. Cl.
CPC .............. *A61F 2002/30281* (2013.01); *A61F 2002/30331* (2013.01); *A61F 2002/30383* (2013.01); *A61F 2002/30477* (2013.01); *A61F 2002/305* (2013.01); *A61F 2002/3052* (2013.01); *A61F 2002/30578* (2013.01); *A61F 2002/30593* (2013.01); *A61F 2002/30604* (2013.01); *A61F 2/30744* (2013.01); *A61F 2002/30841* (2013.01); *A61F 2002/30891* (2013.01); *A61F 2/484* (2021.08); *A61F 2310/00017* (2013.01); *A61F 2310/00023* (2013.01)

(56) References Cited

U.S. PATENT DOCUMENTS

| | | | |
|---|---|---|---|
| 4,805,602 A | | 2/1989 | Puno et al. |
| 4,913,134 A | | 4/1990 | Luque |
| 4,950,269 A | | 8/1990 | Gaines, Jr. |
| 5,127,912 A | | 7/1992 | Ray et al. |
| 5,259,398 A | | 11/1993 | Vrespa |
| 5,300,073 A | | 4/1994 | Ray et al. |
| 5,360,431 A | | 11/1994 | Puno et al. |
| 5,474,555 A | | 12/1995 | Puno et al. |
| 5,522,899 A | | 6/1996 | Michelson |
| 5,558,674 A | | 9/1996 | Heggeness et al. |
| 5,665,122 A | | 9/1997 | Kambin |
| 6,056,749 A | | 5/2000 | Kuslich |
| 6,074,390 A | | 6/2000 | Zucherman et al. |
| 6,102,950 A | * | 8/2000 | Vaccaro ................ A61F 2/4637 |
| | | | 606/247 |
| 6,149,652 A | | 11/2000 | Zucherman et al. |
| 6,179,873 B1 | | 1/2001 | Zientek |
| RE37,161 E | | 5/2001 | Michelson et al. |
| 6,280,444 B1 | | 8/2001 | Zucherman et al. |
| 6,332,882 B1 | | 12/2001 | Zucherman et al. |
| 6,368,351 B1 | | 4/2002 | Glenn et al. |
| 6,419,677 B2 | | 7/2002 | Zucherman et al. |
| 6,432,140 B1 | | 8/2002 | Lin |
| 6,468,276 B1 | | 10/2002 | Mckay |
| 6,478,796 B2 | | 11/2002 | Zucherman et al. |
| 6,485,518 B1 | | 11/2002 | Cornwall et al. |
| 6,527,803 B1 | | 3/2003 | Crozet et al. |
| 6,554,830 B1 | | 4/2003 | Chappius |
| 6,595,998 B2 | | 7/2003 | Johnson et al. |
| 6,613,051 B1 | | 9/2003 | Luk et al. |
| 6,699,247 B2 | | 3/2004 | Zucherman et al. |
| 6,749,595 B1 | | 6/2004 | Murphy |
| 6,796,983 B1 | | 9/2004 | Zucherman et al. |
| 6,811,567 B2 | | 11/2004 | Reiley |
| 6,814,734 B2 | | 11/2004 | Chappius et al. |
| 6,997,929 B2 | | 2/2006 | Manzi et al. |
| 7,114,501 B2 | | 10/2006 | Johnson et al. |
| 7,153,305 B2 | | 12/2006 | Johnson et al. |
| 7,198,627 B2 | | 4/2007 | Bagga et al. |
| 7,234,468 B2 | | 6/2007 | Johnson et al. |
| 7,241,297 B2 | | 7/2007 | Shaolian et al. |
| 7,311,713 B2 | | 12/2007 | Johnson et al. |
| 7,396,360 B2 | | 7/2008 | Lieberman |
| 7,588,590 B2 | | 9/2009 | Chervitz et al. |
| 7,601,157 B2 | | 10/2009 | Boyd et al. |
| 7,611,526 B2 | | 11/2009 | Carl et al. |
| 7,623,902 B2 | | 11/2009 | Pacheco |
| 7,641,658 B2 | | 1/2010 | Shaolian et al. |
| 7,674,278 B2 | | 3/2010 | Manzi et al. |
| 7,686,835 B2 | | 3/2010 | Warnick |
| 7,717,944 B2 | | 5/2010 | Foley et al. |
| 7,727,280 B2 | | 6/2010 | McLuen |
| 7,740,660 B2 | | 6/2010 | Collins et al. |
| 7,744,637 B2 | | 6/2010 | Johnson et al. |
| 7,749,255 B2 | | 7/2010 | Johnson et al. |
| 7,753,912 B2 | | 7/2010 | Raymond et al. |
| 7,780,707 B2 | | 8/2010 | Johnson et al. |
| 7,780,734 B2 | | 8/2010 | Johnson et al. |
| 7,799,034 B2 | | 9/2010 | Johnson et al. |
| 7,799,833 B2 | | 9/2010 | Boyd |
| 7,806,914 B2 | | 10/2010 | Boyd et al. |
| 7,811,331 B2 | | 10/2010 | Johnson et al. |
| 7,815,643 B2 | | 10/2010 | Johnson et al. |
| 7,828,804 B2 | | 11/2010 | Li et al. |
| 7,837,713 B2 | | 11/2010 | Petersen |
| 7,837,733 B2 | | 11/2010 | Collins et al. |
| 7,875,078 B2 | | 1/2011 | Wysocki et al. |
| 7,901,432 B2 | | 3/2011 | Zucherman et al. |
| 7,905,855 B2 | | 3/2011 | Johnson et al. |
| 7,909,871 B2 | | 3/2011 | Abdou |
| 7,909,877 B2 | | 3/2011 | Krueger et al. |
| 7,914,537 B2 | | 3/2011 | Boyd et al. |
| 7,918,877 B2 | | 4/2011 | Zucherman et al. |
| 7,931,688 B2 | | 4/2011 | Landry et al. |
| 7,935,134 B2 | | 5/2011 | Reglos et al. |
| 7,938,818 B2 | | 5/2011 | Yeung |
| 7,963,970 B2 | | 6/2011 | Marino |
| 7,967,867 B2 | | 6/2011 | Barreiro et al. |
| 7,993,375 B2 | | 8/2011 | Bae et al. |
| 8,007,534 B2 | | 8/2011 | Michelson |
| 8,016,829 B2 | | 9/2011 | Mahoney et al. |
| 8,025,680 B2 | | 9/2011 | Hayes et al. |
| 8,066,705 B2 | | 11/2011 | Michelson |
| 8,075,623 B2 | | 12/2011 | Johnson et al. |
| 8,088,163 B1 | | 1/2012 | Kleiner |
| 8,092,533 B2 | | 1/2012 | Melkent |
| 8,096,996 B2 | | 1/2012 | Gutierrez et al. |
| 8,114,092 B2 | | 2/2012 | Altarac et al. |
| 8,123,755 B2 | | 2/2012 | Johnson et al. |
| 8,142,437 B2 | | 3/2012 | McLean et al. |
| 8,162,990 B2 | | 4/2012 | Potash et al. |
| 8,167,887 B2 | | 5/2012 | McLean |
| 8,197,544 B1 | | 6/2012 | Manzi et al. |
| 8,202,274 B2 | | 6/2012 | McLean |
| 8,206,293 B2 | | 6/2012 | Reglos et al. |
| 8,206,395 B2 | | 6/2012 | McLean et al. |
| 8,206,398 B2 | | 6/2012 | Johnson et al. |
| 8,267,969 B2 | | 9/2012 | Altarac et al. |
| 8,317,802 B1 | | 11/2012 | Manzi et al. |
| 8,328,852 B2 | | 12/2012 | Zehavi et al. |
| 8,337,531 B2 | | 12/2012 | Johnson et al. |
| 8,337,532 B1 | | 12/2012 | McLean et al. |
| 8,337,562 B2 | | 12/2012 | Landry et al. |
| 8,343,193 B2 | | 1/2013 | Johnson et al. |
| 8,349,014 B2 | | 1/2013 | Barreiro et al. |
| 8,357,198 B2 | | 1/2013 | McGraw et al. |
| 8,403,934 B2 | | 3/2013 | Angibaud et al. |
| 8,409,208 B2 | | 4/2013 | Abdou |
| 8,414,622 B2 | | 4/2013 | Potash |
| 8,425,571 B2 | | 4/2013 | Bae et al. |
| 8,430,885 B2 | | 4/2013 | Manzi et al. |
| 8,430,913 B2 | | 4/2013 | James et al. |
| 8,450,288 B2 | | 5/2013 | Boyd |
| 8,454,664 B2 | | 6/2013 | McLean |
| 8,460,388 B2 | | 6/2013 | Kirwan et al. |
| 8,475,500 B2 | | 7/2013 | Potash |
| 8,491,639 B2 | | 7/2013 | James et al. |
| 8,512,383 B2 | | 8/2013 | McLean |
| 8,512,409 B1 | | 8/2013 | Mertens et al. |
| 8,523,865 B2 | | 9/2013 | Reglos et al. |
| 8,523,906 B2 | | 9/2013 | McLean et al. |
| 8,535,352 B2 | | 9/2013 | Altarac et al. |

(56) References Cited

U.S. PATENT DOCUMENTS

| | | | |
|---|---|---|---|
| 8,535,353 B2 | 9/2013 | Johnson et al. | |
| 8,545,567 B1 | 10/2013 | Krueger | |
| 8,551,142 B2 | 10/2013 | Altarac et al. | |
| 8,562,654 B2 | 10/2013 | McLean et al. | |
| 8,574,299 B2 | 11/2013 | Barreiro et al. | |
| 8,628,578 B2 | 1/2014 | Miller et al. | |
| 8,641,739 B2 | 2/2014 | McLean et al. | |
| 8,641,767 B2 | 2/2014 | Landry et al. | |
| 8,641,769 B2 | 2/2014 | Malandain | |
| 8,657,826 B2 | 2/2014 | McLean et al. | |
| 8,663,281 B2 | 3/2014 | McLean et al. | |
| 8,702,760 B2 | 4/2014 | Pafford et al. | |
| 8,709,086 B2 | 4/2014 | Glerum | |
| 8,715,351 B1 | 5/2014 | Pinto | |
| 8,727,975 B1 | 5/2014 | Pfabe et al. | |
| 8,740,950 B2 | 6/2014 | McLean et al. | |
| 8,790,375 B2 | 7/2014 | Ali | |
| 8,828,019 B1 | 9/2014 | Raymond et al. | |
| 8,858,635 B2 | 10/2014 | Hovorka et al. | |
| 8,864,830 B2 | 10/2014 | Malandain | |
| 8,894,712 B2 | 11/2014 | Varela | |
| 8,900,312 B2 | 12/2014 | McLean et al. | |
| 8,900,313 B2 | 12/2014 | Barreiro et al. | |
| 8,920,507 B2 | 12/2014 | Malandain | |
| 8,974,464 B2 | 3/2015 | Johnson et al. | |
| 9,039,767 B2 | 5/2015 | Raymond et al. | |
| 9,078,767 B1 | 7/2015 | McLean | |
| 9,084,686 B1 | 7/2015 | McLean et al. | |
| 9,095,446 B2 | 8/2015 | Landry et al. | |
| 9,095,447 B2 | 8/2015 | Barreiro et al. | |
| 9,101,488 B2 | 8/2015 | Malandain | |
| 9,101,489 B2 | 8/2015 | Protopsaltis et al. | |
| 9,107,766 B1 | 8/2015 | McLean et al. | |
| 9,113,962 B2 | 8/2015 | McLean et al. | |
| 9,114,026 B1 | 8/2015 | McLean et al. | |
| 9,119,730 B2 | 9/2015 | Glerum et al. | |
| 9,149,302 B2 | 10/2015 | McLean et al. | |
| 9,192,484 B2 | 11/2015 | Landry et al. | |
| 9,216,094 B2 | 12/2015 | McLean et al. | |
| 9,226,777 B2 | 1/2016 | Potash et al. | |
| 9,237,908 B2 | 1/2016 | Walkenhorst et al. | |
| 9,265,620 B2 | 2/2016 | Ali | |
| 9,265,623 B2 | 2/2016 | McLean | |
| 9,295,565 B2 | 3/2016 | McLean | |
| 9,358,134 B2 | 6/2016 | Malandain | |
| 9,381,094 B2 | 7/2016 | Barreiro et al. | |
| 9,387,089 B2 | 7/2016 | Protopsaltis et al. | |
| 9,398,961 B2 | 7/2016 | Malandain | |
| 9,414,934 B2 | 8/2016 | Cain | |
| 9,414,936 B2 | 8/2016 | Miller et al. | |
| 9,439,692 B1 | 9/2016 | Schlesinger et al. | |
| 9,439,783 B2 | 9/2016 | McLean et al. | |
| 9,445,921 B2 | 9/2016 | McLean | |
| 9,622,873 B2 | 4/2017 | McCormack | |
| 9,861,495 B2 * | 1/2018 | Ali ........................ A61F 2/4455 | |
| 9,980,750 B2 | 5/2018 | Ali | |
| 10,045,857 B2 | 8/2018 | Ali | |
| 10,238,501 B2 | 3/2019 | McCormack et al. | |
| 10,548,742 B2 * | 2/2020 | Ali ........................ A61F 2/4455 | |
| 10,687,962 B2 | 6/2020 | Ali | |
| 10,987,228 B2 | 4/2021 | Ali | |
| 11,304,824 B2 * | 4/2022 | Ali .......................... A61F 2/447 | |
| 11,413,162 B2 | 8/2022 | Ali | |
| 2001/0021852 A1 | 9/2001 | Chappius | |
| 2001/0049527 A1 | 12/2001 | Cragg | |
| 2002/0068976 A1 | 6/2002 | Jackson | |
| 2003/0229346 A1 | 12/2003 | Oribe et al. | |
| 2003/0233145 A1 | 12/2003 | Landry et al. | |
| 2004/0002707 A1 | 1/2004 | Zhao | |
| 2004/0059333 A1 | 3/2004 | Carl et al. | |
| 2004/0092933 A1 | 5/2004 | Shaolian et al. | |
| 2004/0102774 A1 | 5/2004 | Trieu | |
| 2004/0143332 A1 | 7/2004 | Krueger et al. | |
| 2004/0153064 A1 | 8/2004 | Foley et al. | |
| 2004/0186572 A1 | 9/2004 | Lange et al. | |
| 2004/0220582 A1 | 11/2004 | Keller | |
| 2004/0225292 A1 | 11/2004 | Sasso et al. | |
| 2004/0236342 A1 | 11/2004 | Ferree | |
| 2004/0249461 A1 | 12/2004 | Ferree | |
| 2005/0033292 A1 | 2/2005 | Teitelbaum et al. | |
| 2005/0038514 A1 | 2/2005 | Helm et al. | |
| 2005/0049705 A1 | 3/2005 | Hale et al. | |
| 2005/0102027 A1 | 5/2005 | Ferree | |
| 2005/0113842 A1 | 5/2005 | Bertagnoli et al. | |
| 2005/0125066 A1 | 6/2005 | McAfee | |
| 2005/0159746 A1 | 7/2005 | Grob et al. | |
| 2005/0187556 A1 | 8/2005 | Stack et al. | |
| 2005/0197700 A1 | 9/2005 | Boehm et al. | |
| 2005/0228381 A1 | 10/2005 | Kirschman | |
| 2006/0015184 A1 | 1/2006 | Winterbottom et al. | |
| 2006/0036323 A1 | 2/2006 | Carl et al. | |
| 2006/0064107 A1 * | 3/2006 | Bertagnoli ............ A61F 2/4611 | |
| | | | 606/99 |
| 2006/0122701 A1 | 6/2006 | Kiester | |
| 2006/0195097 A1 | 8/2006 | Evans et al. | |
| 2006/0235388 A1 | 10/2006 | Justis et al. | |
| 2006/0235391 A1 | 10/2006 | Sutterlin | |
| 2006/0243287 A1 | 11/2006 | Reuter et al. | |
| 2006/0247771 A1 | 11/2006 | Peterman et al. | |
| 2007/0016221 A1 * | 1/2007 | Beyersdorff .......... A61F 2/4611 | |
| | | | 606/99 |
| 2007/0027545 A1 | 2/2007 | Carls et al. | |
| 2007/0032794 A1 | 2/2007 | Weber et al. | |
| 2007/0032871 A1 | 2/2007 | Michelson | |
| 2007/0050030 A1 * | 3/2007 | Kim ...................... A61F 2/4611 | |
| | | | 623/17.11 |
| 2007/0055257 A1 | 3/2007 | Vaccaro et al. | |
| 2007/0055276 A1 | 3/2007 | Edidin | |
| 2007/0055373 A1 | 3/2007 | Hudgins et al. | |
| 2007/0100454 A1 | 5/2007 | Burgess et al. | |
| 2007/0106383 A1 | 5/2007 | Abdou | |
| 2007/0112428 A1 | 5/2007 | Lancial | |
| 2007/0123891 A1 | 5/2007 | Ries et al. | |
| 2007/0123892 A1 | 5/2007 | Ries et al. | |
| 2007/0149976 A1 | 6/2007 | Hale et al. | |
| 2007/0162032 A1 | 7/2007 | Johnson et al. | |
| 2007/0162044 A1 | 7/2007 | Marino | |
| 2007/0179619 A1 | 8/2007 | Grob et al. | |
| 2007/0250166 A1 | 10/2007 | McKay | |
| 2007/0265561 A1 | 11/2007 | Yeung | |
| 2007/0270858 A1 | 11/2007 | Trieu et al. | |
| 2007/0270968 A1 * | 11/2007 | Baynham ................ A61F 2/447 | |
| | | | 623/17.11 |
| 2007/0288014 A1 | 12/2007 | Shadduck et al. | |
| 2007/0299450 A1 | 12/2007 | Her et al. | |
| 2008/0027437 A1 | 1/2008 | Johnson et al. | |
| 2008/0027454 A1 | 1/2008 | Johnson et al. | |
| 2008/0039947 A1 | 2/2008 | Zucherman et al. | |
| 2008/0058939 A1 | 3/2008 | Hughes et al. | |
| 2008/0234826 A1 | 9/2008 | Chappuis | |
| 2008/0243249 A1 | 10/2008 | Kohm et al. | |
| 2008/0262555 A1 | 10/2008 | Assell et al. | |
| 2008/0319450 A1 | 12/2008 | Corrao | |
| 2009/0005790 A1 | 1/2009 | Pacheco | |
| 2009/0024166 A1 | 1/2009 | Carl et al. | |
| 2009/0062807 A1 | 3/2009 | Song | |
| 2009/0062916 A1 | 3/2009 | Fox | |
| 2009/0076551 A1 | 3/2009 | Petersen | |
| 2009/0076616 A1 | 3/2009 | Duggal et al. | |
| 2009/0082822 A1 | 3/2009 | Osman | |
| 2009/0082870 A1 | 3/2009 | Osman | |
| 2009/0088852 A1 | 4/2009 | Chee | |
| 2009/0105819 A1 | 4/2009 | Barry | |
| 2009/0112269 A1 | 4/2009 | Liberman et al. | |
| 2009/0112320 A1 | 4/2009 | Kraus | |
| 2009/0157119 A1 | 6/2009 | Hale | |
| 2009/0163957 A1 | 6/2009 | St. Clair et al. | |
| 2009/0171393 A9 | 7/2009 | Johnson et al. | |
| 2009/0177205 A1 | 7/2009 | McCormack et al. | |
| 2009/0187191 A1 | 7/2009 | Carl et al. | |
| 2009/0187220 A1 | 7/2009 | Hamada | |
| 2009/0216329 A1 | 8/2009 | Lee et al. | |
| 2009/0234397 A1 | 9/2009 | Petersen | |
| 2009/0248159 A1 | 10/2009 | Aflatoon | |

US 12,575,944 B2

Page 4

(56) References Cited

U.S. PATENT DOCUMENTS

| | | |
|---|---|---|
| 2009/0254186 A1 | 10/2009 | Tornier et al. |
| 2009/0275953 A1 | 11/2009 | Marino et al. |
| 2009/0299412 A1 | 12/2009 | Marino |
| 2009/0306671 A1 | 12/2009 | McCormack et al. |
| 2009/0312764 A1 | 12/2009 | Marino |
| 2010/0004651 A1 | 1/2010 | Biyani |
| 2010/0016903 A1 | 1/2010 | Matityahu et al. |
| 2010/0036495 A1 | 2/2010 | Daum et al. |
| 2010/0100132 A1 | 4/2010 | Pacheco |
| 2010/0114098 A1 | 5/2010 | Carl |
| 2010/0145391 A1 | 6/2010 | Kleiner |
| 2010/0160921 A1 | 6/2010 | Sun et al. |
| 2010/0160922 A1 | 6/2010 | Liu et al. |
| 2010/0168858 A1 | 7/2010 | Hardenbrook et al. |
| 2010/0185289 A1 | 7/2010 | Kirwan et al. |
| 2010/0204795 A1 | 8/2010 | Greenhalgh |
| 2010/0241231 A1 | 9/2010 | Marino et al. |
| 2010/0256619 A1 | 10/2010 | Teitelbaum et al. |
| 2010/0256647 A1 | 10/2010 | Trieu |
| 2010/0280554 A1 | 11/2010 | Vaidya |
| 2010/0292796 A1 | 11/2010 | Greenhalgh et al. |
| 2010/0305700 A1 | 12/2010 | Ben-Arye et al. |
| 2010/0312280 A1 | 12/2010 | Overes et al. |
| 2010/0312346 A1 | 12/2010 | Kueenzi et al. |
| 2010/0324680 A1 | 12/2010 | Suh et al. |
| 2011/0009870 A1 | 1/2011 | Johnson et al. |
| 2011/0028978 A1 | 2/2011 | Li et al. |
| 2011/0112587 A1 | 5/2011 | Patel et al. |
| 2011/0118785 A1 | 5/2011 | Reiley |
| 2011/0118790 A1 | 5/2011 | Reiley |
| 2011/0137421 A1 | 6/2011 | Hansell et al. |
| 2011/0144701 A1 | 6/2011 | Altarac et al. |
| 2011/0144755 A1 | 6/2011 | Baynham et al. |
| 2011/0160772 A1 | 6/2011 | Arcenio et al. |
| 2011/0166603 A1 | 7/2011 | Forrest |
| 2011/0172772 A1 | 7/2011 | Abdou |
| 2011/0172774 A1 | 7/2011 | Varela |
| 2011/0184522 A1 | 7/2011 | Melkent et al. |
| 2011/0213465 A1 | 9/2011 | Landry et al. |
| 2011/0238072 A1 | 9/2011 | Tyndall |
| 2011/0245838 A1 | 10/2011 | Marino |
| 2011/0251647 A1 | 10/2011 | Hale et al. |
| 2011/0251693 A1 | 10/2011 | Barreiro et al. |
| 2011/0264098 A1 | 10/2011 | Cobbs |
| 2011/0264228 A1 | 10/2011 | Johnson et al. |
| 2011/0270261 A1 | 11/2011 | Mast et al. |
| 2011/0276095 A1 | 11/2011 | Bar et al. |
| 2011/0276139 A1 | 11/2011 | Mahoney et al. |
| 2011/0282387 A1 | 11/2011 | Suh et al. |
| 2011/0288588 A1 | 11/2011 | Chin et al. |
| 2011/0288593 A1 | 11/2011 | Bae et al. |
| 2011/0288599 A1 | 11/2011 | Michielli et al. |
| 2011/0307016 A1 | 12/2011 | Reglos et al. |
| 2011/0313462 A1 | 12/2011 | Alleyne |
| 2011/0319941 A1 | 12/2011 | Bar et al. |
| 2012/0010717 A1 | 1/2012 | Spann |
| 2012/0035729 A1 | 2/2012 | Glerum et al. |
| 2012/0046695 A9 | 2/2012 | Blain |
| 2012/0059423 A1 | 3/2012 | Young |
| 2012/0059477 A1 | 3/2012 | Kleiner |
| 2012/0065734 A1 | 3/2012 | Barrett |
| 2012/0083849 A1 | 4/2012 | Neubardt |
| 2012/0089191 A1 | 4/2012 | Altarac et al. |
| 2012/0095509 A1 | 4/2012 | Jensen et al. |
| 2012/0101530 A1 | 4/2012 | Robling et al. |
| 2012/0101582 A1 | 4/2012 | Raiszadeh et al. |
| 2012/0109139 A1 | 5/2012 | Steele |
| 2012/0109317 A1 | 5/2012 | Landry et al. |
| 2012/0116454 A1 | 5/2012 | Edidin |
| 2012/0116459 A1 | 5/2012 | Nottmeier |
| 2012/0123544 A1 | 5/2012 | Shu et al. |
| 2012/0143339 A1 | 6/2012 | Voellmicke et al. |
| 2012/0158003 A1 | 6/2012 | Johnson et al. |
| 2012/0158067 A1 | 6/2012 | Manzi et al. |
| 2012/0158071 A1 | 6/2012 | Jimenez |
| 2012/0158141 A1 | 6/2012 | Johnson et al. |
| 2012/0165871 A1 | 6/2012 | Malone |
| 2012/0172934 A1 | 7/2012 | Fisher et al. |
| 2012/0184993 A1 | 7/2012 | Arambula et al. |
| 2012/0191136 A1 | 7/2012 | Culbert et al. |
| 2012/0209387 A1 | 8/2012 | Lowry et al. |
| 2012/0215259 A1 | 8/2012 | Cannestra |
| 2012/0215312 A1 | 8/2012 | Anderson |
| 2012/0221049 A1 | 8/2012 | Blain |
| 2012/0226318 A1 | 9/2012 | Wenger et al. |
| 2012/0232597 A1 | 9/2012 | Saidha et al. |
| 2012/0239090 A1 | 9/2012 | Abdou |
| 2012/0245637 A1 | 9/2012 | Kraus et al. |
| 2012/0253398 A1 | 10/2012 | Metcalf et al. |
| 2012/0265250 A1 | 10/2012 | Ali |
| 2012/0277753 A1 | 11/2012 | Linderman et al. |
| 2012/0277801 A1 | 11/2012 | Marik et al. |
| 2012/0277862 A1 | 11/2012 | Tornier et al. |
| 2012/0277874 A1 | 11/2012 | Yaun et al. |
| 2012/0283776 A1 | 11/2012 | Mishra |
| 2012/0290014 A1 | 11/2012 | Parent et al. |
| 2012/0290093 A1 | 11/2012 | Hansell et al. |
| 2012/0316566 A1 | 12/2012 | Osman |
| 2012/0316568 A1 | 12/2012 | Manzi et al. |
| 2012/0323326 A1 | 12/2012 | Boehm, Jr. |
| 2013/0006361 A1 | 1/2013 | Glerum et al. |
| 2013/0012994 A1 | 1/2013 | McCormack et al. |
| 2013/0013000 A1 | 1/2013 | Ainsworth et al. |
| 2013/0018467 A1 | 1/2013 | Suh |
| 2013/0023994 A1 | 1/2013 | Glerum |
| 2013/0030469 A1 | 1/2013 | Karas et al. |
| 2013/0035723 A1 | 2/2013 | Donner |
| 2013/0035763 A1 | 2/2013 | Krueger |
| 2013/0041412 A1 | 2/2013 | Moumene |
| 2013/0053892 A1 | 2/2013 | Hawkins et al. |
| 2013/0053893 A1 | 2/2013 | Gamache et al. |
| 2013/0072986 A1 | 3/2013 | Robinson |
| 2013/0079879 A1 | 3/2013 | Suh |
| 2013/0116732 A1 | 5/2013 | Pavlov et al. |
| 2013/0123847 A1 | 5/2013 | Anderson et al. |
| 2013/0123848 A1 | 5/2013 | Duggal et al. |
| 2013/0123927 A1 | 5/2013 | Malandain |
| 2013/0131811 A1 | 5/2013 | Barreiro et al. |
| 2013/0138214 A1 | 5/2013 | Greenhalgh et al. |
| 2013/0144343 A1 | 6/2013 | Arnett et al. |
| 2013/0158667 A1 | 6/2013 | Tabor et al. |
| 2013/0172736 A1 | 7/2013 | Abdou |
| 2013/0172940 A1 | 7/2013 | Skaggs |
| 2013/0178939 A1 | 7/2013 | Poulos |
| 2013/0184758 A1 | 7/2013 | Karim |
| 2013/0197584 A1 | 8/2013 | Currier et al. |
| 2013/0197644 A1 | 8/2013 | Cloutier et al. |
| 2013/0204373 A1 | 8/2013 | Lambrecht |
| 2013/0253650 A1 | 9/2013 | Ashley et al. |
| 2013/0304131 A1 | 11/2013 | McLean et al. |
| 2014/0012385 A1 | 1/2014 | Baynham |
| 2014/0018922 A1 | 1/2014 | Marino et al. |
| 2014/0025113 A1 | 1/2014 | McCormack et al. |
| 2014/0039633 A1 | 2/2014 | Roche et al. |
| 2014/0046333 A1 | 2/2014 | Johnson et al. |
| 2014/0066988 A1 | 3/2014 | McLean et al. |
| 2014/0107788 A1 | 4/2014 | Barreiro et al. |
| 2014/0135936 A1 | 5/2014 | Landry et al. |
| 2014/0163682 A1 | 6/2014 | Lott et al. |
| 2014/0172017 A1 | 6/2014 | McLean et al. |
| 2014/0207239 A1 | 7/2014 | Barreiro |
| 2014/0236296 A1 | 8/2014 | Wagner et al. |
| 2014/0236298 A1 | 8/2014 | Pinto |
| 2014/0277456 A1 | 9/2014 | Kirschman |
| 2014/0277488 A1 | 9/2014 | Davenport |
| 2014/0336468 A1 | 11/2014 | Pfabe et al. |
| 2014/0336471 A1 | 11/2014 | Pfabe et al. |
| 2014/0336764 A1 | 11/2014 | Masson et al. |
| 2015/0045893 A1 | 2/2015 | Dinville et al. |
| 2015/0088257 A1 | 3/2015 | Frostell |
| 2015/0148908 A1 | 5/2015 | Marino et al. |
| 2015/0202051 A1 | 7/2015 | Tanaka et al. |
| 2015/0305887 A1 | 10/2015 | McAtamney et al. |
| 2015/0374354 A1 | 12/2015 | Boyd et al. |

(56)                References Cited

U.S. PATENT DOCUMENTS

| | | |
|---|---|---|
| 2015/0374509 A1 | 12/2015 | Mclean |
| 2016/0007983 A1 | 1/2016 | Frey et al. |
| 2016/0008040 A1 | 1/2016 | McCormack et al. |
| 2016/0015523 A1 | 1/2016 | Lewis et al. |
| 2016/0045333 A1 | 2/2016 | Baynham |
| 2016/0051373 A1 | 2/2016 | Faulhaber |
| 2016/0310291 A1 | 10/2016 | Greenhalgh |
| 2016/0324661 A1 | 11/2016 | Miller et al. |
| 2017/0014243 A1 | 1/2017 | Ali |
| 2017/0112631 A1 | 4/2017 | Kuyler |
| 2017/0119539 A1 | 5/2017 | Glerum et al. |
| 2017/0128108 A1 | 5/2017 | Niemiec et al. |
| 2017/0128226 A1 | 5/2017 | Faulhaber |
| 2017/0128227 A1 | 5/2017 | Huh et al. |
| 2017/0143510 A1 | 5/2017 | Nichols et al. |
| 2017/0165085 A1 | 6/2017 | Lechmann et al. |
| 2017/0172760 A1 | 6/2017 | Loebl et al. |
| 2017/0209282 A1 | 7/2017 | Aghayev et al. |
| 2017/0216050 A1 | 8/2017 | Semler et al. |
| 2017/0224397 A1 | 8/2017 | Grimberg et al. |
| 2017/0231769 A1 | 8/2017 | De Villiers et al. |
| 2017/0319352 A1 | 11/2017 | Dewey et al. |
| 2017/0333199 A1 | 11/2017 | Sharifi-Mehr et al. |
| 2017/0340358 A1 | 11/2017 | Bullard |
| 2017/0348464 A1 | 12/2017 | Wecker et al. |
| 2017/0354512 A1 | 12/2017 | Weiman et al. |
| 2018/0042731 A1 | 2/2018 | Bannigan |
| 2018/0092669 A1 | 4/2018 | Donner et al. |
| 2018/0092751 A1 | 4/2018 | Vrionis et al. |
| 2018/0092754 A1 | 4/2018 | Jang et al. |
| 2018/0110628 A1 | 4/2018 | Sharifi-Mehr et al. |
| 2018/0116817 A1 | 5/2018 | Weiman et al. |
| 2018/0296359 A1 | 10/2018 | Sack |
| 2018/0353303 A1 | 12/2018 | Ali |
| 2019/0117266 A1 | 4/2019 | Ali |
| 2019/0133783 A1 | 5/2019 | Unger et al. |
| 2019/0209338 A1 | 7/2019 | Ali |
| 2019/0231551 A1 | 8/2019 | Freedman et al. |
| 2019/0254838 A1 | 8/2019 | Miller et al. |
| 2019/0314040 A1 | 10/2019 | Greenhalgh et al. |
| 2020/0163776 A1 | 5/2020 | Ali |
| 2021/0137696 A1 | 5/2021 | Ali |
| 2022/0079772 A1 | 3/2022 | Ali |
| 2022/0218493 A1 | 7/2022 | Ali |
| 2022/0218496 A1 | 7/2022 | Hopson et al. |
| 2023/0112704 A1 | 4/2023 | Ali |
| 2025/0134673 A1 | 5/2025 | Ali |

FOREIGN PATENT DOCUMENTS

| | | |
|---|---|---|
| RU | 2 345 729 | 2/2009 |
| RU | 2 391 061 | 6/2010 |
| RU | 2 377 961 | 10/2010 |
| WO | WO 1998/048717 | 11/1998 |
| WO | WO 2006/020464 | 2/2006 |
| WO | WO 2006/065774 | 6/2006 |
| WO | WO 2009/006622 | 1/2009 |
| WO | WO 2009/143496 | 11/2009 |
| WO | WO 2010/056355 | 5/2010 |
| WO | WO 2010/064234 | 6/2010 |
| WO | WO 2011/155931 | 12/2011 |

OTHER PUBLICATIONS

Extended European Search Report for European patent application No. 14773239.0 (the EPO National Stage application of PCT/US2014/025035) dated Sep. 2, 2016.

* cited by examiner

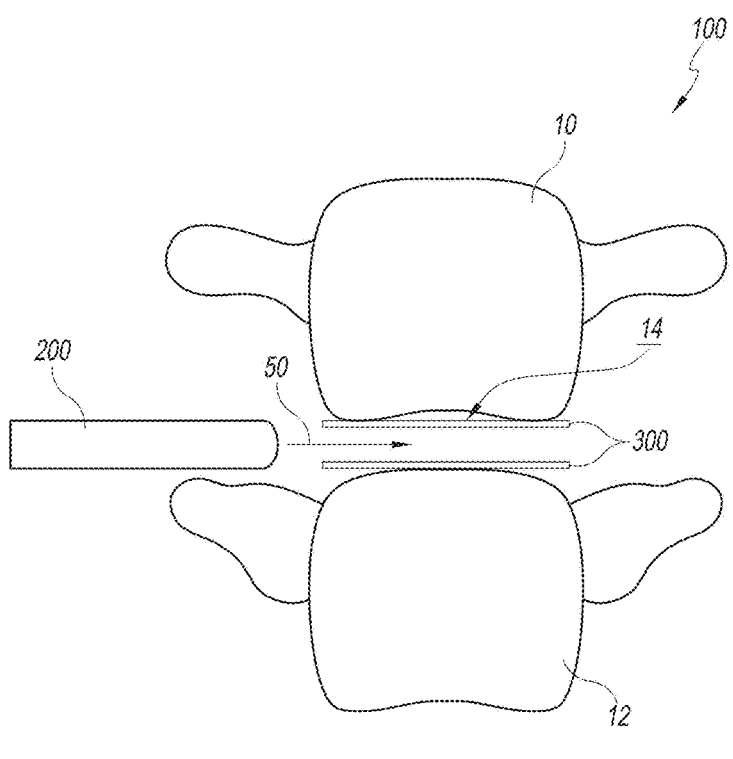
FIG. I
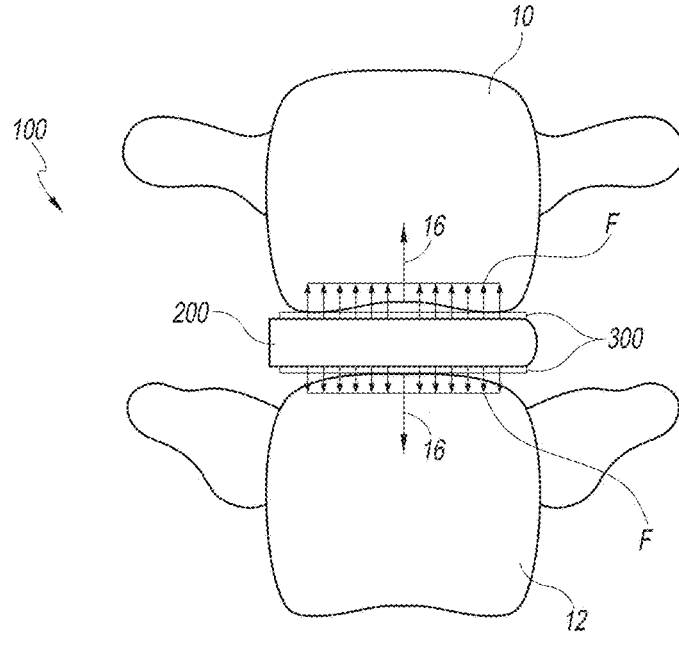
FIG. 2

INTERBODY FUSION DEVICES, SYSTEMS AND METHODS

CROSS-REFERENCE TO RELATED APPLICATIONS

This application is a continuation of U.S. patent application Ser. No. 16/779,289 filed Jan. 31, 2020, which is a continuation of U.S. patent application Ser. No. 15/865,154 filed Jan. 8, 2018 and issued as U.S. Pat. No. 10,548,742 on Feb. 4, 2020, which is a continuation of U.S. patent application Ser. No. 14/774,640 filed Sep. 10, 2015 and issued as U.S. Pat. No. 9,861,495 on Jan. 9, 2018, which is the U.S. National Phase under 35 U.S.C. § 371 of International Application PCT/US2014/025035 filed Mar. 12, 2014, titled Lateral Interbody Fusion Devices, Systems and Methods, which claims priority benefit under 35 U.S.C. § 119(e) of U.S. Provisional Application No. 61/786,160, filed Mar. 14, 2013. The entireties of all of the foregoing are hereby incorporated by reference herein.

BACKGROUND

Field

This application relates generally to devices, systems and methods for the treatment of the spine, and more specifically, to spinal implants and related tools, systems and methods.

Description of the Related Art

Surgical approaches to the intervertebral space are utilized for a variety of indications and purposes, such as, for example, biopsy (e.g., for evaluation of possible infection, other pathology, etc.), discectomy (e.g., for decompression of nerve roots, to prepare for subsequent fusion procedures, etc.), disc height restoration or deformity correction, disc replacement or repair (e.g., annular repair), discogram, gene therapy and/or other procedures or treatments.

Various approaches are currently used to access the inter-body or intervertebral space of a patient's thoracic, lumbar and sacral spine. These include anterior approaches (ALIF) (e.g., open, mini-open retroperitoneal, etc.), lateral approaches (e.g., costotranversectomy, extreme lateral, etc.), posterolateral approaches (e.g., posterior lumbar interbody fusion (PLIF), transforaminal lumbar interbody fusion (TLIF), etc.) and axial approaches (e.g., axial lumbar interbody fusion). Further, many minimally invasive and percutaneous approaches rely on radiographic landmarks with or without direct view to access a targeted interbody space. In addition, many, if not all, of these currently used approaches require violation of the disc annulus to access the disc space.

Fusion surgery of the thoracic, lumbar and sacral spine is often performed for a variety of indications, including degenerative joint disease, deformity, instability and/or the like. Typically, traditional fusion approaches involve relatively large, open incisions performed under direct vision. Minimally invasive surgical techniques and corresponding surgical implants have become more popular in an attempt to reduce morbidity and generally improve outcomes. Multiple variations of percutaneous systems (e.g., pedicle screw and rod systems, facet screw systems, etc.) have been developed. Such systems can allow for instrumentation placement with fluoroscopic guidance (e.g., using radiographically recognizable body landmarks) and/or other imaging technologies. Current fusion techniques, including those that utilize open and minimally invasive approaches, often require direct visualization. However, such techniques typically involve traversing spaces that are occupied by neural elements. Thus, these neural elements need to be retracted or otherwise moved during the execution of spinal procedures that precede implantation (e.g., annulotomy, discectomy, disc space and/or vertebral endplate preparation, etc.). Retraction of sensitive neural elements can also be required during the delivery of an implant to the spine.

These approaches typically require contact and retraction of nerve roots and/or sensitive visceral organs, blood vessels and/or other sensitive portions of the anatomy. Contact and retraction of these structures can place them at risk, thereby increasing the likelihood of complications and damage to a patient. Accordingly, a need exists for improved approaches for spinal fusion and/or access to intervertebral spaces.

SUMMARY

According to some embodiments, a method of inserting an implant within an intervertebral space defined between an upper vertebral member and a lower vertebral member comprises positioning a plate system within the intervertebral space, wherein the plate system comprises an upper plate and a lower plate, and advancing an implant between the upper plate and the lower plate so that the implant is urged into the intervertebral space, the upper plate engages the upper vertebral member, and the lower plate engages the lower vertebral member, wherein upon advancement of the implant between the upper and lower plates, the upper vertebral member is distracted relative to the lower vertebral member.

According to some embodiments, advancing an implant between the upper and lower base plates comprises using a device or tool (e.g., mechanical tool, pneumatic tool, etc.). In one embodiment, advancing the implant between the upper plate and the lower plate comprises advancing the implant at least partially through a guiding assembly (e.g., between upper and lower members of the assembly). In one embodiment, the guiding assembly is removably secured and/or aligned with the upper and lower plates.

According to some embodiments, the guiding assembly comprises upper and lower guiding members or plates, wherein the upper and lower guiding members or plates are configured to removably engage corresponding portions of the upper and lower plates when the implant is advanced into the intervertebral space. In some embodiments, advancing the implant between the upper and lower plates deploys at least one engagement member or feature of at least one of the upper plate or the lower plate, wherein the at least one engagement member or feature is configured to engage at least a portion of the an adjacent vertebral member. In some embodiments, the at least one engagement member or feature comprises a tooth, spike, barb and/or the like.

According to some embodiments, the implant is configured to be advanced between the upper and lower plates using a rail system. In one embodiment, the rail system comprises at least one protruding member or feature on the implant and at least one corresponding groove or recess on the upper plate or lower plate, wherein the at least one protruding member or feature is configured to (e.g., slidably or otherwise) move within the at least one corresponding groove or recess on the upper plate or lower plate. In some embodiments, the rail system comprises at least one groove or recess on the implant and at least one corresponding protruding member or feature on the upper plate or lower plate, wherein the at least one protruding member or feature is configured to (e.g., slidably or otherwise) move within the at least one corresponding groove or recess.

According to some embodiments, the implant comprises a generally smooth outer surface. In some embodiments, the implant does not comprise any teeth or other engagement features. In some embodiments, the implant comprises PEEK, stainless steel, titanium, other metals or alloys, other polymeric materials and/or the like.

According to some embodiments, the upper and lower plates comprise at least one metal or alloy and/or a poly- meric material (e.g., PEEK). In some embodiments, the at least one metal or alloy comprises titanium, stainless steel and/or any other medical grade metal or alloy. In some embodiments, the lower plate and/or the upper plate is bead-blasted or is otherwise at least partially roughened (e.g., along one or more surfaces that are configured to contact and engage native vertebral tissue of the subject). In some embodiments, the lower plate and/or the upper plate comprises an ingrowth surface (e.g., along one or more surfaces that are configured to contact and engage native vertebral tissue of the subject).

According to some embodiments, the method further comprises securing at least one screw or other fastener through an opening of the implant (and/or an adjacent plate, washer or other member) after the implant has been properly secured within the intervertebral space. In some embodi- ments, the at least one screw passes through at least a portion of the upper or lower plate. In some embodiments, the at least one screw passes through at least a portion of the upper or lower vertebral member (and/or an adjacent plate, washer or other member).

According to some embodiments, the method further comprises creating a passage (e.g., lateral passage) through a subject in order to provide minimally invasive access to the intervertebral space. In one embodiment, the method further comprises clearing out native tissue of the subject within and/or near the intervertebral space (e.g., using one or more rasps and/or other native tissue removal tools or methods).

According to some embodiments, a spinal fusion system comprises a plate system configured for placement within an intervertebral space of a subject, wherein the plate system comprises an upper plate and a lower plate, an implant configured to be advanced and positioned between the upper plate and the lower plate to secure the implant within the intervertebral space, wherein, when the implant is advanced between the upper plate and the lower plate, the upper plates engages the upper vertebral member, and the lower plate engages the lower vertebral member, and wherein, upon advancement of the implant between the upper and lower plates, the upper vertebral member is distracted relative to the lower vertebral member.

According to some embodiments, the system additionally comprises a guiding assembly having upper and lower slides, wherein the upper slide is configured to removably couple to the upper plate, and wherein the lower slide is configured to removably couple to the lower plate. In one embodiment, the upper plate and/or the lower plate com- prises at least one engagement member (e.g., tooth, spike, barb, etc.) configured to engage a portion of the adjacent vertebral member when the implant has been advanced between the upper and lower plates.

According to some embodiments, the implant is config- ured to be advanced between the upper and lower plates using a rail system. In one embodiment, the rail system comprises at least one protruding member or feature on the implant and at least one corresponding groove or recess on the upper plate or lower plate, wherein the at least one protruding member or feature is configured to slidably move within the at least one corresponding groove or recess on the upper plate or lower plate. In some embodiments, the rail system comprises at least one groove or recess on the implant and at least one corresponding protruding member or feature on the upper plate or lower plate, wherein the at least one protruding member or feature is configured to slidably move within the at least one corresponding groove or recess.

According to some embodiments, the implant comprises a generally smooth outer surface. In one embodiment, the implant does not comprise any teeth or other engagement features. In some embodiments, the implant comprises PEEK, titanium and/or any other metal, alloy and/or poly- meric material. In one embodiment, the upper and lower plates comprise at least one metal (e.g., titanium, stainless steel, etc.), alloy and or polymeric material (e.g., PEEK).

According to some embodiments, the system further comprises at least one screw or other fastener, the screw or fastener being configured to be secured through an opening of the implant after the implant has been properly secured within the intervertebral space. In one embodiment, the at least one screw passes through at least a portion of the upper or lower plate. In some embodiments, the screw passes through at least a portion of the upper or lower vertebral member.

According to some embodiments, a method of inserting a lateral implant within an intervertebral space defined between an upper vertebral member and a lower vertebral member includes creating a lateral passage through a subject in order to provide minimally invasive access to the interver- tebral space, at least partially clearing out native tissue of the subject within and/or near the intervertebral space, position- ing a base plate within the intervertebral space, wherein the base plate comprise an upper base plate and a lower base plate and advancing an implant between the upper base plate and the lower base plate so that the implant is urged into the intervertebral space and the upper vertebral member is distracted relative to the lower vertebral member.

According to some embodiments, advancing an implant between the upper and lower base plates comprises using a mechanical device (e.g., a threaded-system using a rotatable handle to advance a rod or other actuator, manual or mechanically-assisted device, etc.). In some embodiments, the implant comprises at least one groove and at least one of the upper base plate member and the lower base plate member comprises at least one protruding feature, the at least one groove being configured to align and move relative to the at least one protruding feature. In some embodiments, the implant is delivered through the base plate using a rail or other alignment system. In some embodiments, the implant comprises at least one of PEEK, titanium and/or the like. In some embodiments, the base plate comprises titanium, stain- less steel or another medically-acceptable metal or alloy.

According to some embodiments, the method further includes securing at least one screw (e.g., 1, 2, 3, 4, more than 4, etc.) through an opening of the implant after the implant has been properly secured within the intervertebral space. In one embodiment, the screw also passes through at least a portion of the upper or lower base plate member and/or the upper or lower vertebra.

The methods summarized above and set forth in further detail below describe certain actions taken by a practitioner; however, it should be understood that they can also include the instruction of those actions by another party. Thus, actions such as "advancing an implant" include "instructing advancing an implant."

BRIEF DESCRIPTION OF THE DRAWINGS

These and other features, aspects and advantages of the present application are described with reference to drawings of certain embodiments, which are intended to illustrate, but not to limit, the present inventions. It is to be understood that these drawings are for the purpose of illustrating the various concepts disclosed herein and may not be to scale.

FIG. 1 schematically illustrates one embodiment of a spinal implant system with the implant not positioned within the target intervertebral space;

FIG. 2 illustrates the system of FIG. 1 with the implant positioned between the base plate members and implanted within the intervertebral space;

DETAILED DESCRIPTION

Figure 3A:
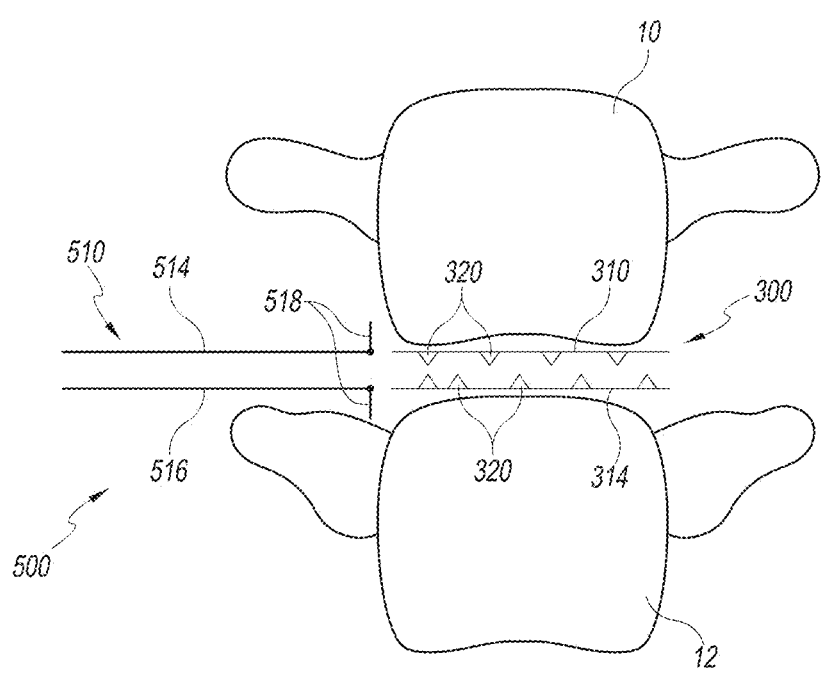
FIGS. 3A and 3B illustrate various views of a base plate of an implant system according to one embodiment.

A variety of examples described below illustrate various configurations that may be employed to achieve desired improvements. The particular embodiments and examples are only illustrative and not intended in any way to restrict the general concepts presented herein and the various aspects and features of such concepts.

According to some embodiments, the present application discloses various devices, systems and methods for accessing the intervertebral or interbody space of a patient's spine and/or performing certain procedures related to spinal fusion using minimally invasive surgery (MIS) techniques. As discussed in greater detail herein, the intervertebral or interbody space of the targeted portion of the patient's spine is accessed and/or treated minimally invasively using, at least in some embodiments, a lateral approach. The terms "intervertebral space" and "interbody space" are used interchangeably herein, and generally refer to the space, gap or region between adjacent vertebral members. By way of example, as illustrated in FIG. 1, the intervertebral space 14 between adjacent vertebrae 10, 12 can be accessed using one or more lateral openings or passages created laterally through the subject's anatomy (e.g., using one or more access device, such as, retractors, dilators, etc.). In some embodiments, such openings or passages are created, accessed and/or otherwise use using MIS techniques or procedures. The various devices, systems and methods disclosed herein, and variations thereof can be applied to any type of spinal implant, including, but not limited to, a lateral interbody fusion implant, a transforaminal lumbar interbody fusion (TLIF) implant, an oblique TLIF implant, a posterior lumbar interbody fusion (PLIF) implant, an anterior lumbar interbody fusion (ALIF) implant and/or the like. Accordingly, the various embodiments disclosed herein can be in a variety of MIS or non-MIS approaches, including, without limitation, lateral, TLIF, posterior, ALIF and/or the like.

FIG. 1 schematically illustrates one embodiment of a spinal fusion or stabilization system 50. As shown, the system 50 can include upper and lower plates (e.g., endplate members) 300 or other members that are positioned along the endplates of the upper and lower vertebral members 10, 12. In some embodiments, the plates 300 generally extend across the entire or substantially the entire width of the vertebrae 10, 12. In some embodiments, the plates 300 are the same length or substantially the same length as the spinal implant 200 that will be delivered between the plates 300 and into the intervertebral space 14. For example, the plates 300 and/or the implant 200 can be approximately 40 to 60 mm long (e.g., 40, 45, 50, 55, 60 mm, lengths between the foregoing ranges, etc.). In other embodiments, however, the length of the implant is greater than 60 mm or less than 40 mm, as desired or required.

According to some embodiments, the upper and lower plates comprise at least one metal or alloy and/or a polymeric material (e.g., PEEK). In some embodiments, the at least one metal or alloy comprises titanium, stainless steel and/or any other medical grade metal or alloy. In some embodiments, the lower plate and/or the upper plate is bead-blasted or is otherwise at least partially roughened (e.g., along one or more surfaces that are configured to contact and engage native vertebral tissue of the subject). In some embodiments, the lower plate and/or the upper plate comprises an ingrowth surface (e.g., along one or more surfaces that are configured to contact and engage native vertebral tissue of the subject). In some arrangements, such a configuration can assist to prevent movement between the plate and the vertebral body.

Figure 9A:
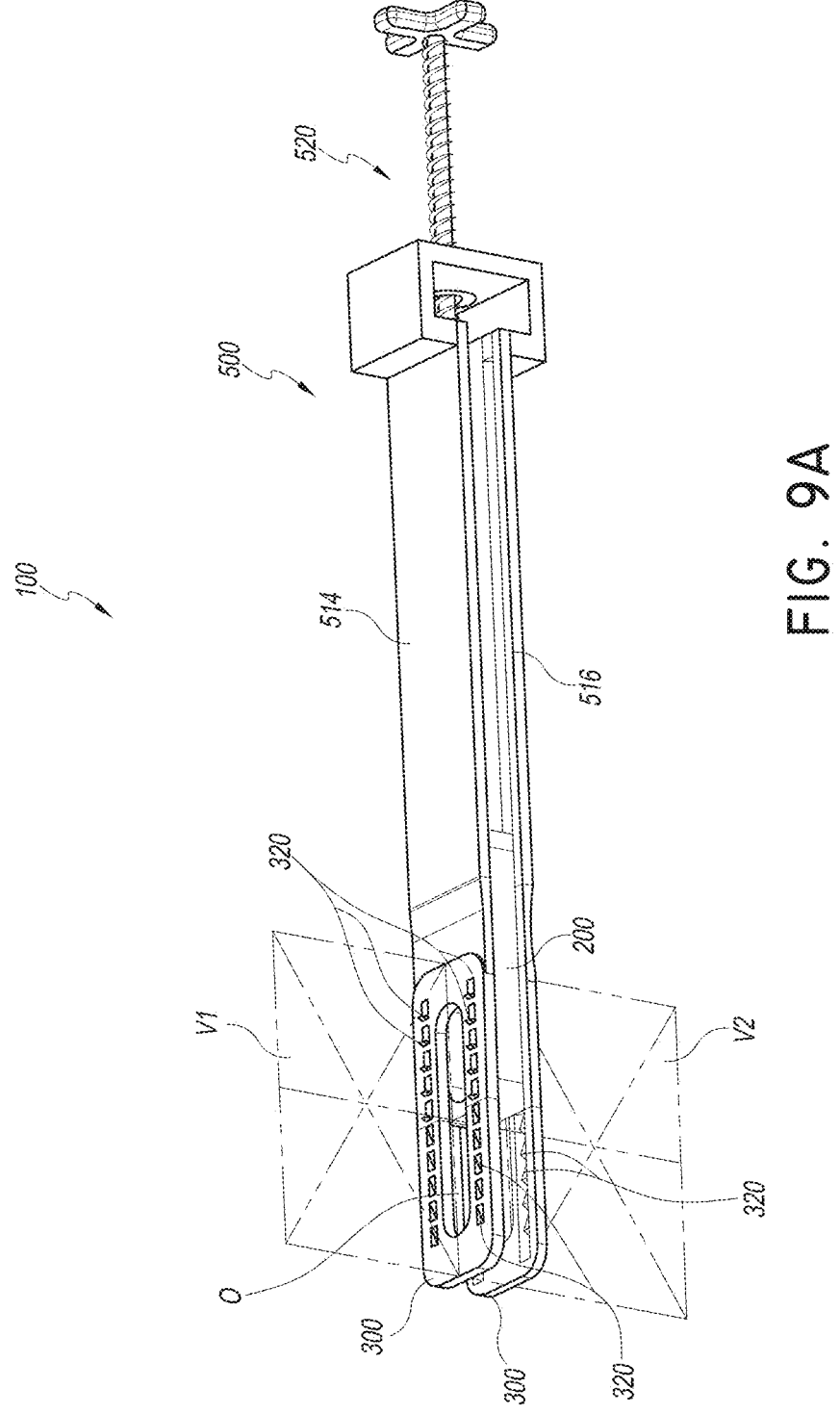
FIGS. 9A-9D illustrate different views of a fusion system according to one embodiment.

In some embodiments, as illustrated in FIG. 9A, each of the upper and lower plates 300 comprises at least one central opening O that can at least partially align with and provide access to (e.g., from a space generally between the upper and lower plates) to native tissue of the adjacent vertebral members V1, V2 of the subject.

In some embodiments, once the plates (e.g., endplate members) 300 have been properly positioned within the target intervertebral space 14, the implant 200 can be delivered (e.g., laterally) between the upper and lower plates or other members 300. The delivery of the implant 200 between the plates 300 can be performed with or without the use of a mechanical delivery tool (e.g., by using a threaded delivery device or other device providing for mechanical advantage, etc.). Regardless of the exact manner in which the implant 200 is advanced into the intervertebral space 14 between the upper and lower plates 300, the upper and lower plates 300 can provide one or more advantages or benefits. For example, the use of the plates 300 can help distribute forces and moments along a larger surface area. This is generally illustrated by the schematic force distribution diagram F in FIG. 2. Accordingly, the likelihood of potentially damaging localized forces, moments and/or other stresses on a particular portion or area of the adjacent vertebrae 10, 12 can be reduced or eliminated. The risk of damage to bone and/or other native tissues to the subject during a fusion procedure can be further reduced by advancing the implant 200, and thus separating the upper and lower plates 300 in a more predictable, gentler manner (e.g., as opposed to traditional methods of using great force to position an implant within a target intervertebral space).

Further, in some embodiments, the use of the upper and lower plates 300 can facilitate the delivery of the implant 200 within the target interbody space with greater ease and less resistance. As a result, the endplates and other portions of the adjacent vertebrae 10, 12 can be protected against shearing, fractures and/or other damage. This can be especially important when the implant 100 causes distraction (e.g., separation or opening) of a collapsed or partially collapsed interbody space 14, as represented by the arrows 16 in FIG. 2.

As discussed herein, one or both sides of the upper and/or lower plates can include spikes, teeth, other protruding members and/or other engagement features. For example, if such engagement features are positioned along the top of the upper plate or the bottom of the lower plate, the engagement features can be advanced into the adjacent endplate(s) as the implant 200 is moved between the plates 300. This can help secure the plates to the adjacent vertebrae 10, 12. In some embodiments, engagement features can be positioned along the opposite surfaces of the plates (e.g., along the bottom of the upper plate and/or along the top of the lower plate). Such engagement features can help prevent or reduce the likelihood of relative movement between the implant 200 and the plates 300 following implantation. In other embodiments, as discussed in greater detail herein with reference to, e.g., FIGS. 9A to 12, the implant 200 and the adjacent surfaces of the upper and lower plates 300 can include recesses, protrusions, other components of a "rail" system and/or any other feature to help maintain a particular orientation between the plates and the implant during use and/or after implantation, to help prevent or reduce the likelihood of any undesirable relative movement between the plates and the implant during use and/or after implantation and/or the like. Thus, the plates and/or the implant can include one or more other features, such as, for example, rails or guiding members (e.g., to assist in moving the implant more easily and more predictably between the plates), tabs or other portions configured to receive one or more screws or other fasteners (e.g., to further secure the system 100 to the spine after delivery into the intervertebral space) and/or the like.

Figure 3B:
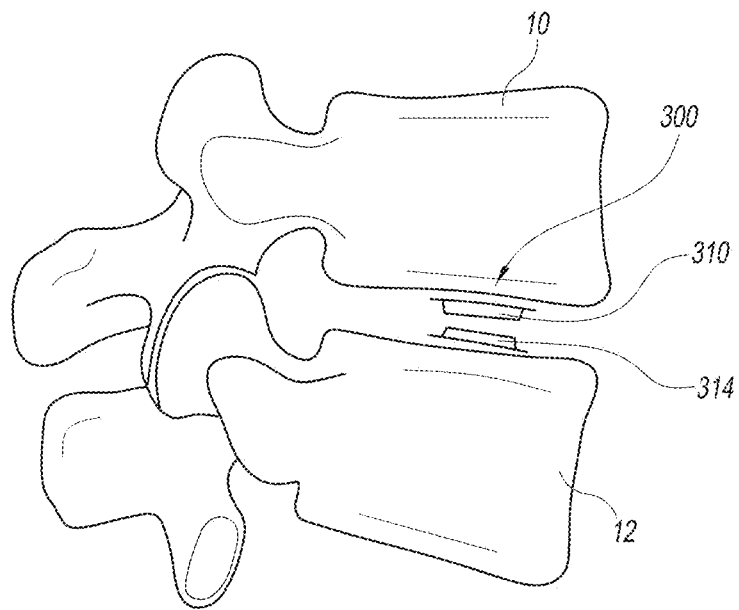

FIGS. 3A and 3B illustrate different views of one embodiment of upper and lower plates (e.g., base plates or endplate members) 300 configured for use in a spinal fusion system. As shown, the base plates 300 can include upper and lower plates 310, 314. The base plates 300 can be shaped, sized and configured to span across an entire width of the subject's vertebrae 10, 12. As discussed herein, the upper and/or lower plates can include one or more openings to provide access to the adjacent native vertebral surfaces of the subject after implantation. In some embodiments, the base plates 300 extend beyond one or more side of the vertebral periphery or do not extend to the lateral edge of the vertebrae (e.g., are short by a certain clearance distance from one or more lateral edges of the vertebrae). In some embodiments, where the plates 300 extend beyond a perimeter of the upper and/or lower vertebrae, a portion of the plate 300 can be configured to be removed or manipulated after implantation. For example, in some embodiments, in such a configuration, a protruding portion of the plate can be folded or bent (e.g., either upwardly or downwardly) to move the folded or bent portion either toward or away from the intervertebral space. In some embodiments, such a bent or folded portion can include one or more openings or other holes that can be used to place a bone screw of other fastener therethrough (e.g., to secure that portion of the plate to an adjacent vertebral member, to another bent or folded plate used in a fusion system, to a separate washer or other plate member and/or the like.

As shown in FIG. 3A, the plate members 310, 314 can include one or more protruding members (e.g., teeth, rails, other engagement members or features, etc.) 320 that extend toward each other (e.g., toward the intervertebral space). Such protruding members can be fixed or movable. For example, in some embodiments, the protruding members 320 are deployable (e.g., before, during or after advancement of an implant between the base plates 300). In other embodiments, plate members 300 can include teeth, protruding members or other engagement features or devices along their opposite surfaces (e.g., along the top of the upper plate, along the bottom of the lower plate, etc.), either in lieu of or in addition to having inwardly-directed protruding members. As discussed in greater detail herein, outwardly-projecting protruding members 320 on the plates (e.g., FIG. 9A) can help secure the plates to the adjacent surfaces of the upper and lower vertebral members of the subject being treated. This can advantageously provide one or more clinical benefits, such as, for example, the preservation of long-term implantation (e.g., reducing the likelihood of dislodgement or movements of the implant system within the target intervertebral space following implantation).

With continued reference to FIG. 3A, a system can include a guiding assembly 500 that can be strategically positioned along one of the lateral ends of the targeted intervertebral space. The guiding assembly 500 can include an alignment device 510 that may comprise one or more alignment components 514, 516. Regardless of its exact configuration and design, the alignment device 510 can advantageously permit a surgeon or other practitioner to accurately position the guiding assembly 500 for the subsequent delivery of an implant therethrough and between the base plates 300. As discussed in greater detail herein, the guiding assembly 500 can include upper and lower alignment members or slide members 514, 516, which are generally aligned with the upper and lower plates 300. In some embodiments, each alignment member 514, 516 can be configured to removably attach to the corresponding plate 300 to help advance and position the plates 300 within the targeted intervertebral space (e.g., minimally invasively). In some embodiments, the distal ends of the alignment members or slides 514, 516 can be configured to be slidably received within slots, recesses or other portions of the plates 300. Thus, the guiding assembly 500 can be temporarily coupled to the plates when the plates are being advanced into the intervertebral space and when the implant is subsequently delivered between the plates (e.g., as discussed in greater detail below). However, in some embodiments, once the implant 200 has been properly advanced between the plates and the implant system has been adequately secured between the adjacent vertebrae, the alignment members or slides 514, 516 can be easily retracted (e.g., rearwardly or proximally) relative to the plates and implant for removal from the subject's anatomy and completion of the fusion procedure.

With continued reference to FIG. 3A, the alignment members or components 514, 516 and/or one or more other portions or components of the assembly can include a flange or other abutment or securement portion 518. Such a flange 518 can be fixedly or movable positioned along the adjacent vertebrae 10, 12 of the subject to ensure proper alignment into the targeted intervertebral space. In other arrangements, as noted herein, the alignment members and other components of the guiding assembly are configured to completely decouple from the plates and the implant after implant has been properly delivered into the target intervertebral space.

Figure 4:
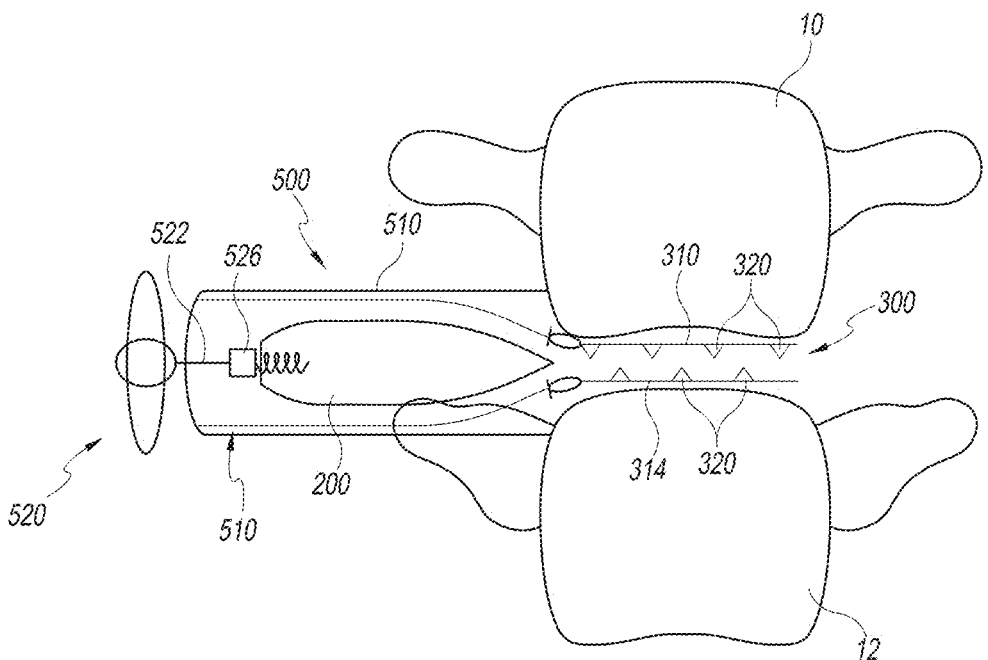
FIG. 4 illustrates a side view of a spinal implant system according to one embodiment.

As illustrated in FIG. 4, an implant 200 can be delivered between the plates 300 and into the intervertebral space using a mechanical advancement device. Therefore, in some embodiments, the guiding assembly 500 can advantageously comprise a mechanical advancement device or feature. For example, in FIG. 4, the guiding assembly comprises a threaded delivery portion that is configured to advance an implant 200 between the base plate members 310, 314 by turning a rotatable handle or other advancement tool. As a user rotates the handle 520, a rod 522 or other actuator is moved forwardly (e.g., distally) in the direction of the implant 200. The implant 200 can be directly or indirectly coupled to the actuator 522 via one or more coupling or other detachable connections 526, as desired or required. As the rod is advanced distally, the implant (e.g., lateral cage) can be guided between the base plate members 310, 314 and into the intervertebral space. Consequently, the base plate members 310, 314 separate and are urged toward the adjacent endplates of the vertebrae. In some embodiments, as illustrated schematically in FIG. 4, the implant can include a taper (e.g., bullet design) along its distal end to facilitate initial entry and subsequent distraction and separation of the base plate 300.

In other embodiments, one or more other devices can be used to help advance the implant between the plates. For example, a pneumatic tool (e.g., air or liquid driven tool) can be used to apply the required force on the implant to move it into position. Any other type of user-assisting device or system can be used to help advance the implant between the plates, such as, for example, other types of mechanical devices, electromechanical devices, motorized devices, pumps and/or the like.

With continued reference to FIG. 4, the guiding assembly 500 can include one or more structures 510 that help ensure that the implant stays within the guiding assembly 500 and maintains its alignment with the intervertebral space during advancement between the plates. Such structure 510 can, for example, help reduce any deflection or misdirection of the implant's leading end during distal delivery to the intervertebral space, especially when relatively high forces are being exerted on the implant (e.g., that may otherwise cause the implant to move out of alignment with the base plates). In some embodiments, the implant 200, the base plates 300 and/or any other portion of the system can include rails or other alignment features that further help maintain a proper alignment of the implant during advancement between a subject's vertebrae. As discussed in greater detail herein, the guiding assembly can include alignment members (e.g., slides) 514, 516 that removably secure to the plates 300 and provide a reliable and predictable path for advancement of the implant within the intervertebral space. In some embodiments, such slides 514, 516 can be subsequently removed and decoupled or separated (e.g., slidably, mechanically, etc.) from the plates 300.

Figure 5A:
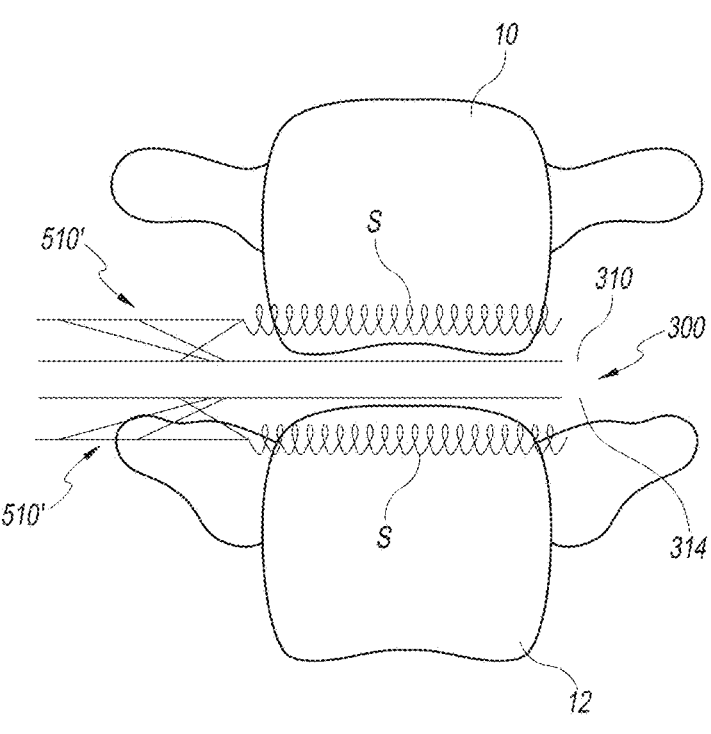
FIGS. 5A-5C illustrate various views of one embodiment of a base plate for use in a spinal implant system.
Figure 5B:
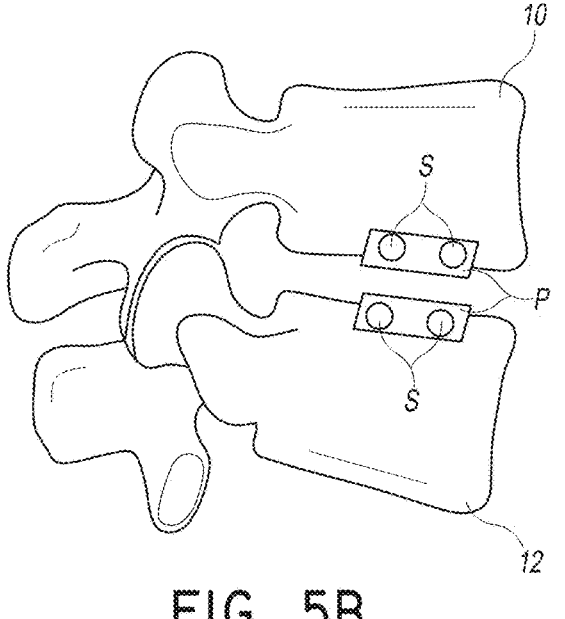
Figure 5C:
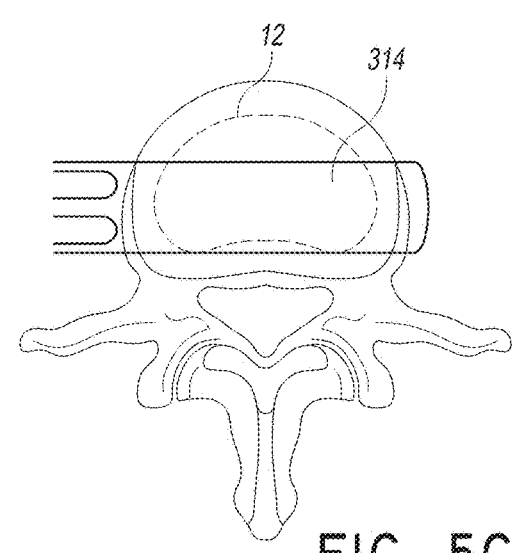

FIGS. 5A-5C illustrate various views of a different embodiment of a system comprising base plates 300 for receiving a spinal implant. As shown, an alignment device 510' can be positioned relative to one or more of the adjacent vertebrae 10, 12 and subsequently secured thereto using additional fasteners or other connection devices or methods. For example, one or more screws S or other fasteners can be used to secure one or more portions of the alignment device to the upper and/or lower vertebral members of the subject. In some embodiments, the alignment devices 510' comprise one or more flanges or plates P through which the screws S or other fasteners can be placed. Once the alignment device 510' has been secured to the subject, the implant can be delivered between the base plate members 310, 314. The alignment device 510', base plate 300 and/or other portions of the system can be left in place after the implant has been secured between the subject's vertebrae. In other embodiments, however, one or more components of the system (e.g., base plate 300, screws, etc.) can be left in place after implantation, and in some instances, may help reinforce or otherwise benefit the treated area.

Figure 6A:
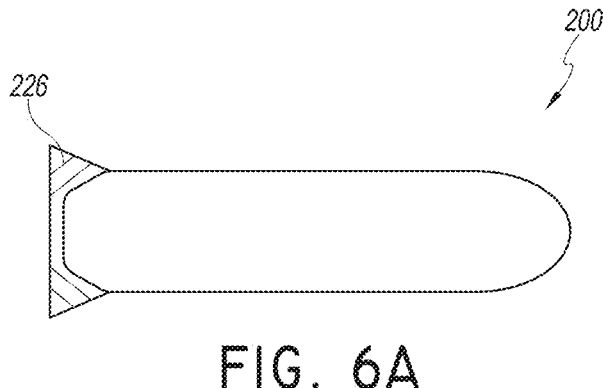
FIGS. 6A and 6B illustrate various views of one embodiment of an implant configured for use in a spinal implant system.
Figure 6B:
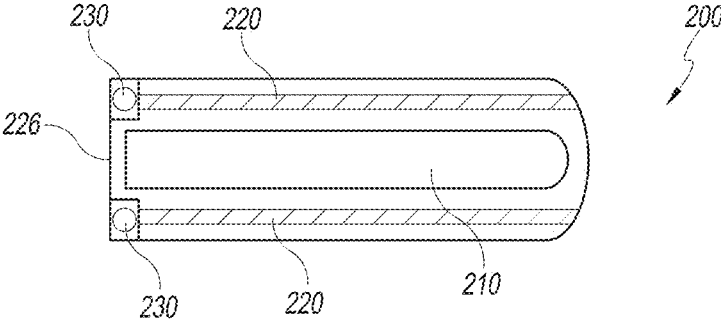

One embodiment of an implant 200 that can be used with the spinal fusion systems disclosed herein is illustrated in FIGS. 6A and 6B. As best shown in the top view of FIG. 6B, the implant 200 can include one or more open regions or chambers 210 for holding a grafting material. In addition, the implant can include one or more grooves 220 or other recesses along its anterior and/or posterior walls. In some embodiments, such grooves 220 or other features can align and mate with corresponding rails, protrusions or features of the base plate 300. Accordingly, the grooves, rails and/or other features can help safely, accurately and predictably move the implant 200 into the target intervertebral space (e.g., between adjacent base plate members). In other embodiments, however, the rail system between the implant 200 and the adjacent plates 300 can be reversed. For example, as illustrated in the embodiments of FIGS. 9A to 16, the implant can include one or more protruding or raised portions that generally align and correspond to grooves or recesses along the adjacent surfaces of the plates 300. Regardless of the exact orientation and design of the rail system, such a system can help ensure that an implant is accurately and safely delivered to a target intervertebral space.

In some embodiments, the implants disclosed herein comprise PEEK, titanium or other acceptable materials. For example, in some embodiments, the implant 200 comprises a metal edge plate or other surface or feature 226 through which one or more screws (not shown in FIGS. 6A and 6B) can be subsequently delivered to secure the implant 200 to one or more of the subject's vertebrae. In some arrangements, the plate 226, which can be positioned along the proximal end of the implant 200, comprises titanium or other acceptable metal or alloy and/or other rigid or semi-rigid material.

Figure 7A:
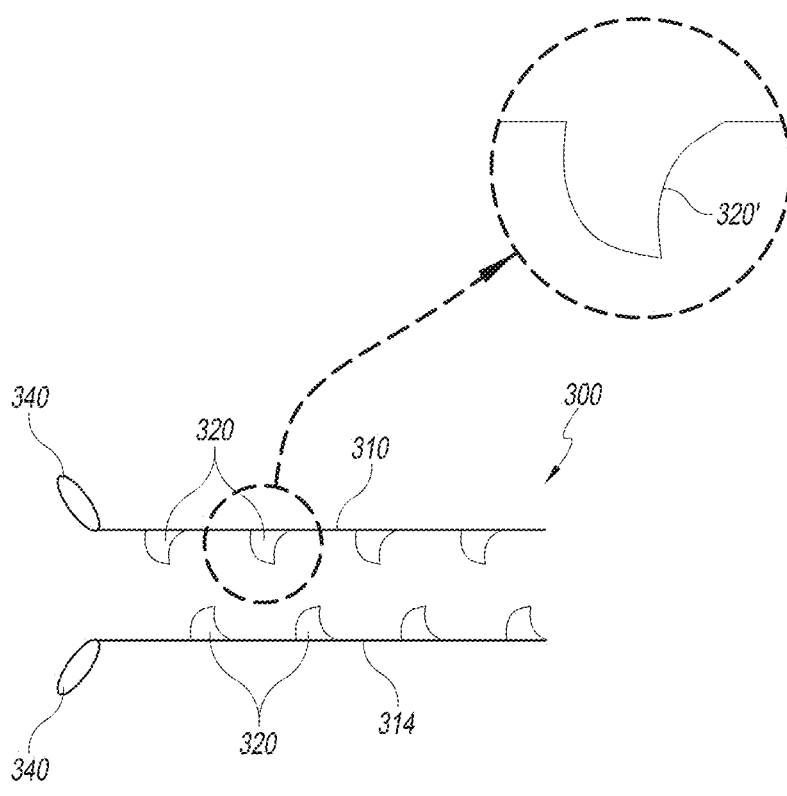
FIG. 7A illustrates one embodiment of a base plate configured for use in a spinal implant system.

FIG. 7A illustrates a side view of one embodiment of a base plate 300 comprising upper and lower plate members 310, 314. As shown, the base plate members 310, 314 can include one or more protruding members 320. Such protruding members 320 can include tabs, bumps, spikes, teeth, grasping members, engagement members, other sharp, smooth and/or rounded features or members and/or the like. In some embodiments, the protruding members 310, 314 can be fixed (e.g., non-movable, non-deployable, etc.) and/or movable (e.g., selectively retractable, deployable, etc.). For example, in some embodiments, the protruding members 320 of the upper and/or lower plate members 310, 314 are deployable using a mechanical connection, a temperature change and/or using some other mechanism of action, device or method. In some embodiments, such protruding members 320 can help engage the plates 300 to the implant 200. In other embodiments, however, the protruding members 320 can be configured to reverse their orientation (e.g., in a direction away from the interior of the intervertebral space or toward the adjacent vertebral member) when the implant is advanced over the protruding members during implantation. Therefore, in some embodiments, as the implant is advanced between the plates 300, the protruding members 320 can deform or otherwise change orientation so as to engage the upper and lower vertebral members. This can provide positive engagement of the plates into the adjacent vertebrae, which may, in some circumstances, result in a more secure implantation of the system within the subject.

Figure 7B:
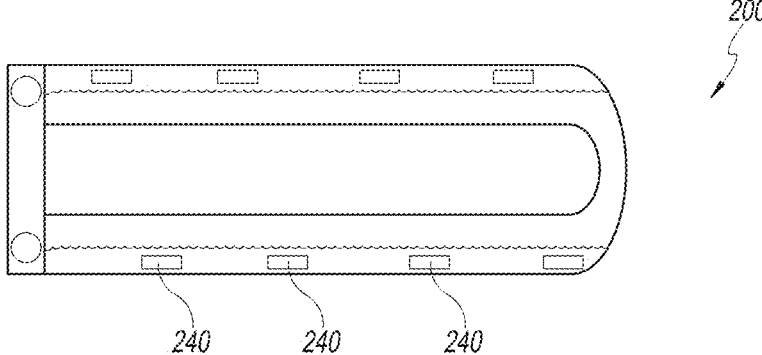
FIG. 7B illustrates one embodiment of an implant configured to be used together with the base plate of FIG. 7A.

FIG. 7B illustrates a top view of one embodiment of an implant 200 that is configured to be used with the base plate 300 of FIG. 7A. Specifically, as shown, the implant 200 can include one or more grooves, holes, recesses or other openings 240 that are shaped, sized and otherwise config- ured to receive corresponding protruding members 320 of the base plate 300. As discussed in greater detail herein, in other arrangements (e.g., FIG. 9A), an implant 200 can include one or more protruding members or features that are sized, shaped and otherwise configured to engage and move within grooves or corresponding recesses of the adjacent plates 300.

With continued reference to FIG. 7B, the protruding members 320' of the base plate 300 can include a curved leading edge to permit the groove 240 of the implant 200 to only temporarily engage the member 320' as the implant is advanced into the target intervertebral space. Thus, the protruding members can sequentially engage and disengage a groove on the implant (e.g., in a ratcheting manner). In some embodiments, the implant can only be permitted to be advanced in one direction (e.g., distally). Such an embodi- ment can be helpful when using base plates 300 that have fixed protruding members 320. In embodiments comprising deployable protruding members, the need for such ratchet- ing system (e.g., that permits movement in at least one direction) may not be needed, as the protruding members 320 can be selectively deployed only when the implant is properly positioned between the base plate members.

In some embodiments, the use of protruding members and corresponding grooves or other recesses can help with guiding an implant 200 between adjacent base plate mem- bers (e.g. during delivery). Such embodiments can also assist in securely maintaining the implant in its implanted position following the delivery of the implant in the target intervertebral space.

Figure 8A:
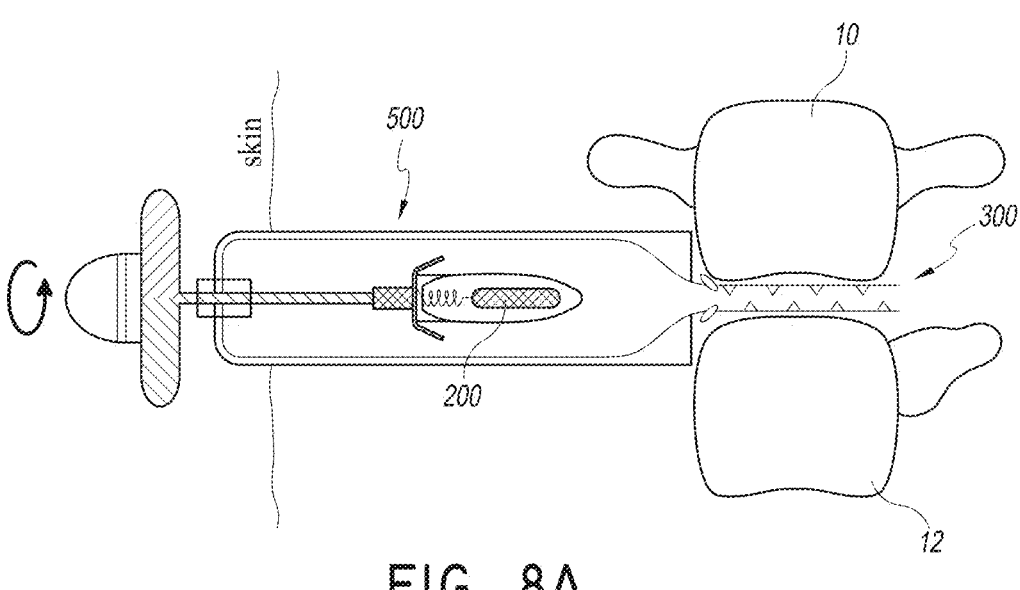
FIGS. 8A-8C illustrate various time-sequential side views during a spinal implant procedure according to one embodiment.
Figure 8B:
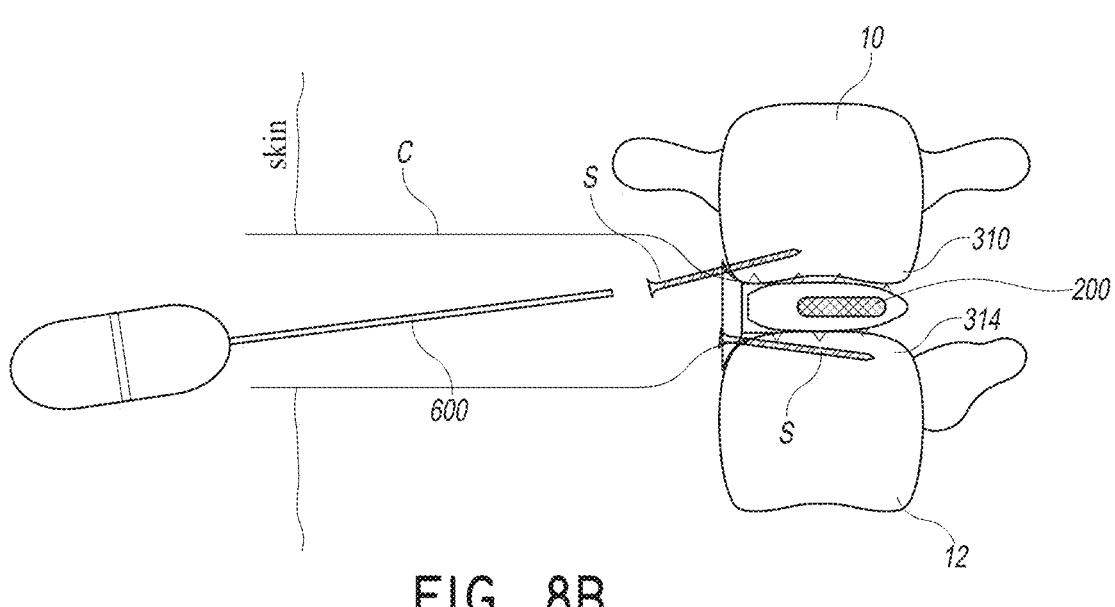
Figure 8C:
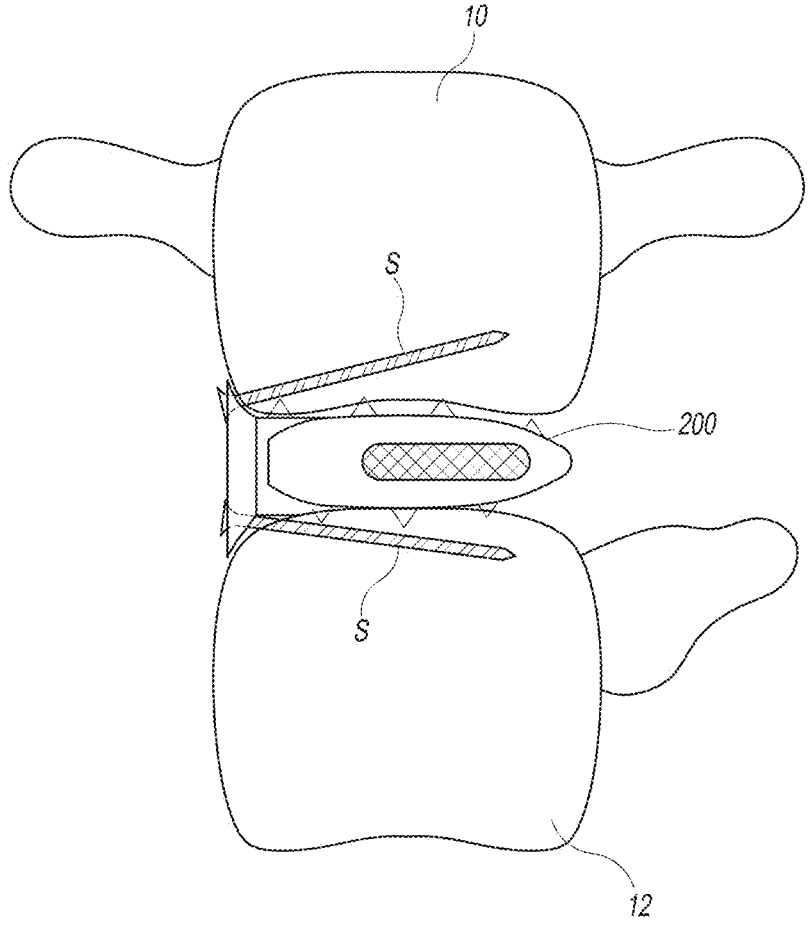

As illustrated schematically in FIGS. 8A-8C, a lateral implant device in accordance with the various embodiments disclosed herein, can be delivered to the target intervertebral space minimally invasively (e.g., through one or more tissue dilators, cannulas or other openings). As discussed in greater detail herein, once the plates 300 have been properly posi- tioned between the subject's vertebrae 10, 12, a guiding assembly 500 can be positioned through a dilator or other access device and in general alignment with the targeted intervertebral space. The implant can be advanced using a mechanical device (as illustrated in FIG. 8A), manually and/or using some other method or device. Further, the implant and base plate can include one or more features or members (e.g., rails, grooves, etc.) to assist in accurately moving the implant in the desired anatomical location of the subject's spine. Once the implant has been advanced between the base plate members 310, 314 and properly within the intervertebral space, the guiding assembly 500 can be removed.

With reference to FIG. 8B, in some embodiments, a screwdriver or other mechanical device 600 can be delivered through a dilator, cannula or other access device C to engage and advance one or more screws S or other fasteners through corresponding openings along the proximal end of the implant 200. In some embodiments, the use of such fasteners can assist with maintaining the position of the implant 200 relative to the subject's spine following implantation, as shown in FIG. 8C. The screws S can be routed through the implant, the base plate and/or the vertebra, as desired or required. However, in other embodiments, the use of screws S or other fasteners is not needed or required to maintain the implanted implant between the base plate members and the adjacent vertebrae. In some embodiments, a total of four fixation screws are positioned through the proximal end of the implanted implant (e.g., two above and two below). In some embodiments, the screws or other fasteners can be passed through openings of one or more plates or washers that at least partially cover or otherwise shield the interver- tebral space, provide additional structural support and/or provide one or more other benefits or advantages. In other embodiments, more or fewer screws or other fasteners can be used, as desired or required.

In order to remove disk material, cartilage, endplate or other vertebral tissue and/or native tissue of a subject during an implantation procedure, a surgeon or other practitioner can use any of the rasping or other tissue cutting devices and methods disclosed in U.S. patent application Ser. No. 13/422,816, titled TRANSPEDICULAR ACCESS TO INTERVERTEBRAL SPACES AND RELATED SPINAL FUSION SYSTEMS AND METHODS, filed Mar. 16, 2012 and published as U.S. Publ. No. 2012/0265250 on Oct. 18, 2012, and U.S. Provisional Patent Application No. 61/783, 839, titled DEVICES AND METHODS FOR TRANS- PEDICULAR STABILIZATION OF THE SPINE and filed on Mar. 14, 2013, the entireties of both of which are hereby incorporated by reference herein and made a part of the present application.

FIGS. 9A-9D illustrate different views of another embodi- ment of a spinal fusion system 100. As discussed above with reference to other arrangements, the system 100 can include upper and lower plates 300 that are sized, shaped and otherwise configured to be positioned between the adjacent vertebral members V1, V2 where fusion is targeted. The system 100 further comprises a guiding assembly 500. In some embodiments, as discussed above, the alignment mem- bers (e.g., slides) 514, 516 of the guiding assembly 500 are configured to releasably secure or otherwise temporarily engage to or with the plates 300. Accordingly, the plate-slide assembly can be placed within the subject and advanced to the target intervertebral space. For example, in some embodiments, one or more distal portions of the alignment members or slides 514, 516 can releasably attach to and/or slide within adjacent portion(s) of the plates 300. In other embodiments, such as the system 100A illustrated in FIG. 14, one or both of the slides 514A, 516A comprise an extension portion 518A that extends into the targeted intervertebral space and provides a surface over which the implant can move when the implant is advanced in the vicinity of the vertebral members. The use of such extension portion 518A can help maintain the graft material within the interior chambers of the implant during advancement to the intervertebral space. Accordingly, the use of extension portions 518A or similar members or features can be advantageously incorporated into any implant system embodiments disclosed herein or equivalents thereof.

With continued reference to FIGS. 9A-9D, the system 100 can comprise a delivery device or feature 520 that can facilitate the surgeon or other practitioner with the advancement of the implant 200 through the guiding assembly and into the intervertebral space (e.g., between the plates 300). In some embodiments, the implant 200 is initially inserted at or near the proximal end of the guiding assembly 500, generally between the alignment members or slides 514, 516. Then, once the surgeon has advanced the guiding assembly 500, and in some configurations, the plates 300 and the implant 200 to which the assembly 500 is engaged, through the subject's anatomy (e.g., through an access device), the surgeon can begin to move the implant distally by manipulating the handle or other portion of the guiding assembly.

Figure 9B:
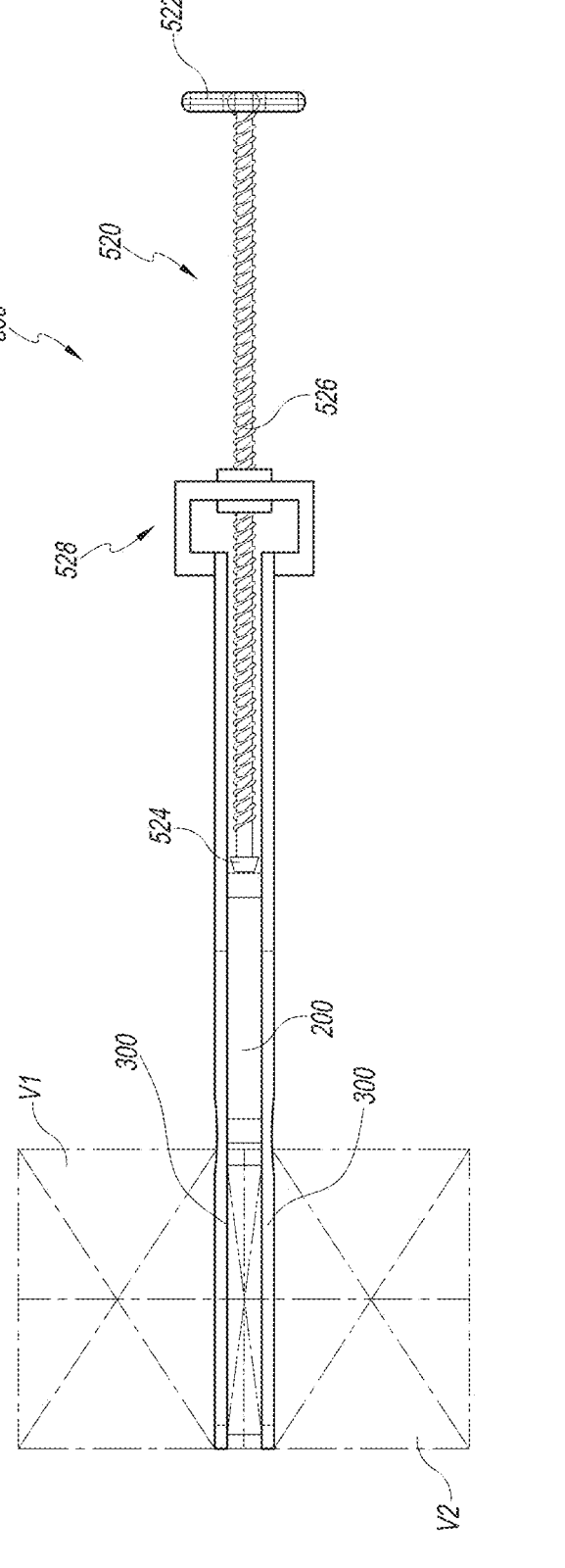
Figure 9C:
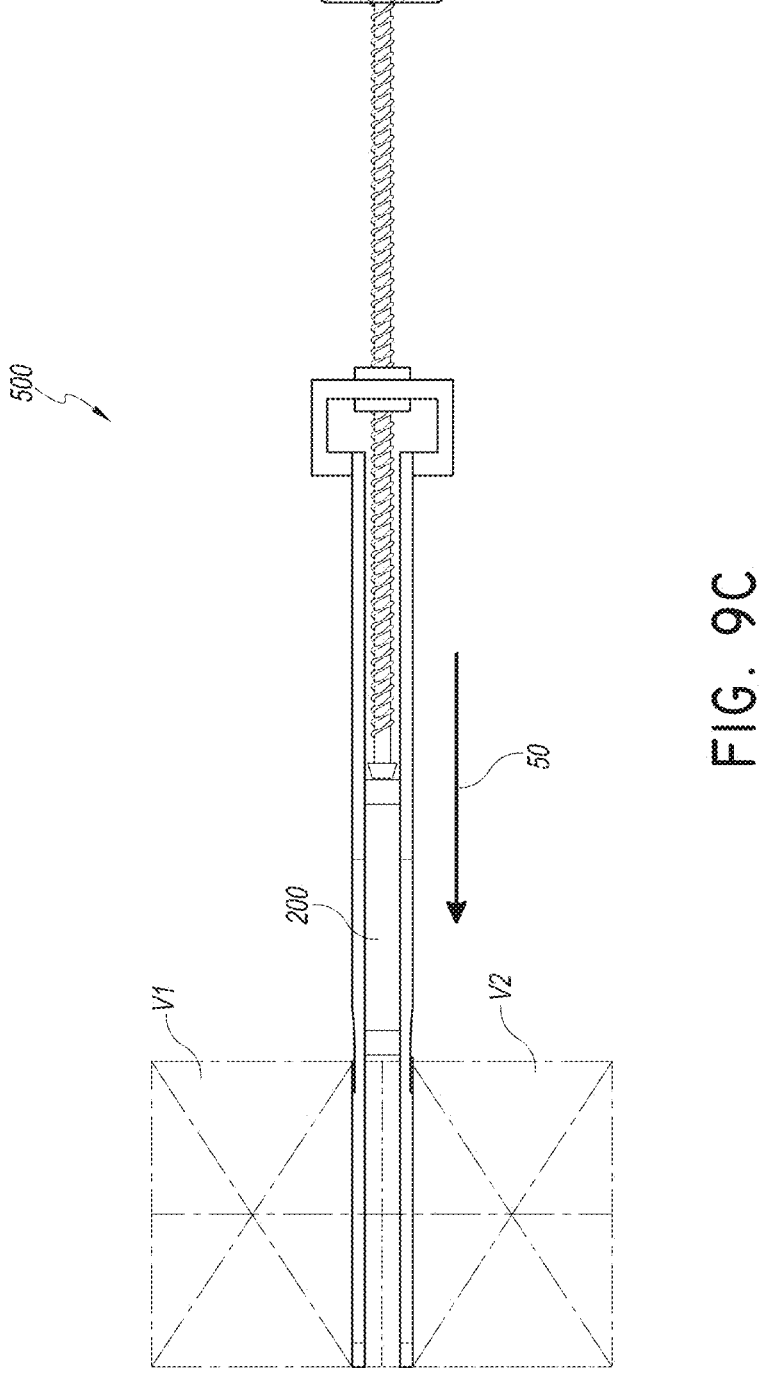
Figure 9D:
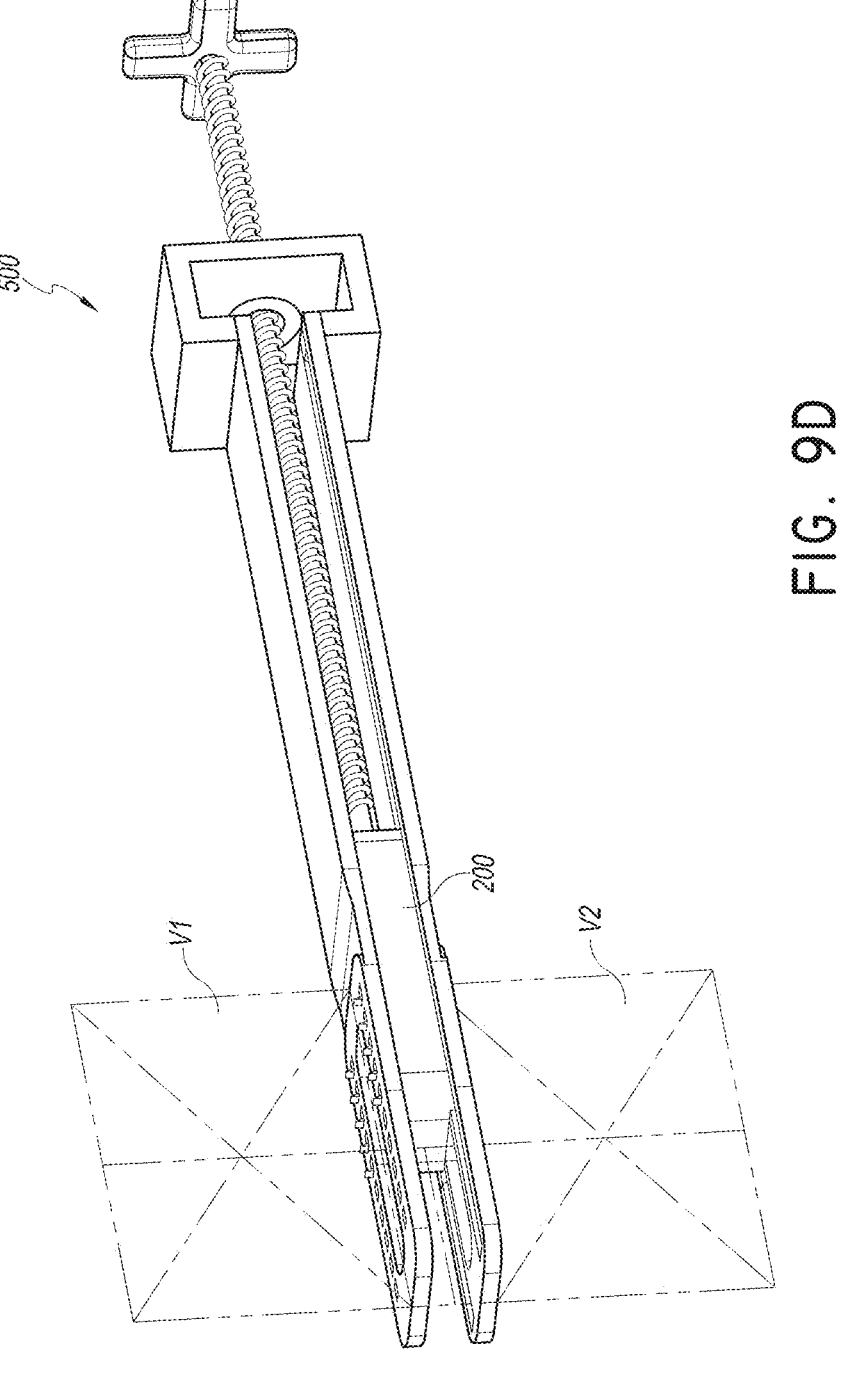

For example, with reference to the side view of FIG. 9B, by turning the handle 522 of the guiding assembly 500, the threaded rod 526 can move relative to a housing 528. Such manipulation of the handle 522 can result in moving the distal end 524 of the rod 526 forwardly (e.g., distally) so as to engage the implant 200 positioned between the slides 514, 516 and exert a force on the implant 200. In some embodiments, the distal end 524 of the rod comprises a coupling or other blunt member or feature that can help avoid damage to the adjacent portion of the implant 200 during the advancement process.

As illustrated in FIG. 9A, as the implant is advanced distally within the interior of the guiding assembly 500 (e.g., between the upper and lower slides or alignment members 514, 516), the distal end of the implant 200 will reach the proximal end of the plates 300 that have been positioned within the intervertebral space. With continued advancement of the implant 200 in the distal direction (e.g., as schematically represented by arrow 50 in FIG. 9C), the implant 200 will move between the upper and lower plates 300, causing the plates 300 to separate apart from each other, in certain arrangements. In some configurations, the implant 200 is moved far enough distally between plates 200 so that is spans across an entire length or substantially an entire length of the plates 300.

Figure 10A:
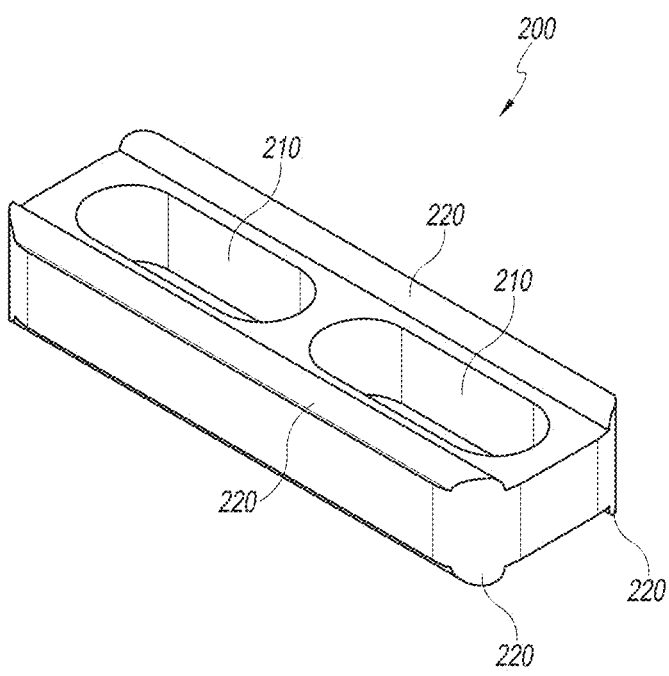
FIGS. 10A and 10B illustrate different views of one embodiment of an implant configured for use with a spinal fusion system.
Figure 10B:
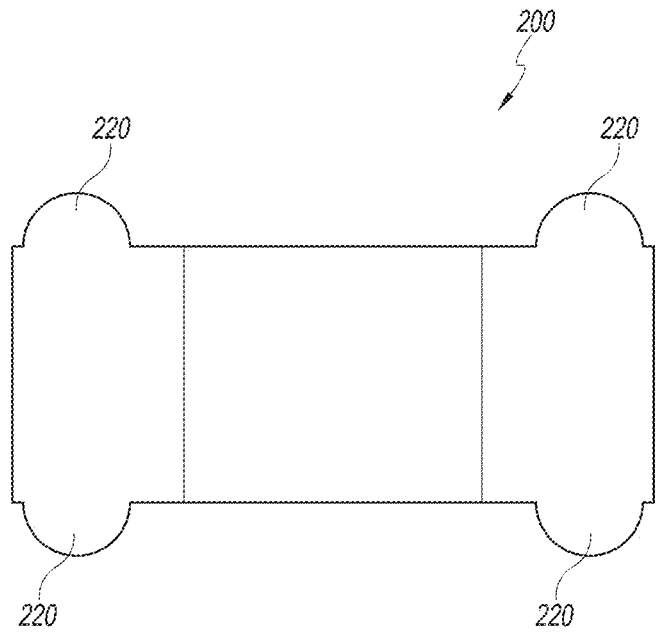

FIGS. 10A and 10B illustrate one embodiment of an implant 200 that is configured to be used with one or more of the fusion systems disclosed herein, including the system 100 of FIGS. 9A-9D. As shown, the implant 200 can include one or more internal chambers 210. Such chambers 210 can be sized, shaped and otherwise configured to be at least partially filled with graft material (not shown) before the implant 200 is advanced between the plates 300. As noted above, the implant 200 can comprise one or more materials, such as, for example, PEEK, titanium, other metals or alloys, other polymeric materials and/or the like.

Figure 11:
FIG. 11 illustrates a partial cross-sectional view of an implant positioned within a guiding assembly and upper and lower plates, according to one embodiment.

With continued reference to FIGS. 10A and 10B, the implant 200 can include one or more protrusions, ridges or similar members or features 220 that extend at least partially along one or more surfaces of the implant 200. In some embodiments, such protrusions 220 can be sized, shaped and otherwise configured to be moved relative to corresponding grooves or recesses of the upper and lower plates 300 and/or the upper and lower slides or alignment members 514, 516 of the guiding assembly 500. For example, as shown in the embodiment of FIG. 11, the upper plate and/or the lower plate 300 can include one or more grooves or recesses 320 that are configured to receive the protrusions 220 of the implant 200 when the implant is properly positioned within the guiding assembly 500 and between the plates 300. Although not illustrated in the view of FIG. 11, the grooves or recesses 320 can extend proximal to the plates 300 and be present, either continuously or intermittently along at least a portion of the slides 514, 516 of the guiding assembly 500. Thus, the implant 200 can be predictably moved between the slides 514, 516 and the plates 300 to properly, safely and securely position the implant 200 within a targeted intervertebral space.

In the embodiments illustrated herein, the guiding assembly 500 and the plates 300 are generally straight, and the path that the implant follows through the guiding assembly 500 is generally linear. However, in other embodiments, the grooves or recesses of the guiding assembly and/or the plates (and thus, the corresponding protruding members or features of the implant 200), or vice versa, can be at least partially curved, so that the implant is moved along a non-linear pathway. In some embodiments, the non-linear pathway can comprise a continuous curve (e.g., with a constant or variable diameter along the length of the curve). However, in other arrangements, the curve or turn is more abrupt (e.g., piecemeal turn or short radius turn) so as to avoid a longer, sweeping turning radius. Such embodiments can be helpful with certain MIS approaches where an implant needs to be maneuvered more carefully and precisely around sensitive nerve structures, such as, for example, in a TLIF procedure.

In the embodiments of a "rail" system illustrated in FIGS. 10A, 10B and 11 herein, and discussed in greater detail above, the implant comprises generally smooth outer surfaces (e.g., does not comprises teeth or other engagement features). Since the implant will not directly contact or engage the adjacent surfaces of the vertebral members, the need for teeth, other protruding members and/or other roughened surface features may not be necessary. This can advantageously simplify the design, manufacturability, cost and other aspects of the implant.

In the illustrated embodiments, the implant includes generally rounded protruding members or features 220 along both of its lateral ends and along both its upper and lower surfaces. Further, the protruding features 220 are generally continuous along an entire length of the implant 200. However, in other embodiments, the implant 200 can include more or fewer protruding features 220. The protruding features 220 can include any desired cross-sectional shape or configuration (e.g., rounded, circular, oval, rectangular, triangular, other polygonal, irregular, etc.), as desired or required. Further, the protruding features 220 can extend only partially or intermittently along one or both surfaces of the implant 200. Thus, the total number of protruding members 220 (e.g., and thus, corresponding grooves or recesses in the plates 300 and guiding assembly 500) can be less or more than four (e.g., 1, 2, 3, 4, 5, 6, 7, 8, 9, 10, more than 10, etc.), as desired or required. For example, in some arrangements, the protruding members 220 are included only the top or the bottom of the implant 200.

Figure 12:
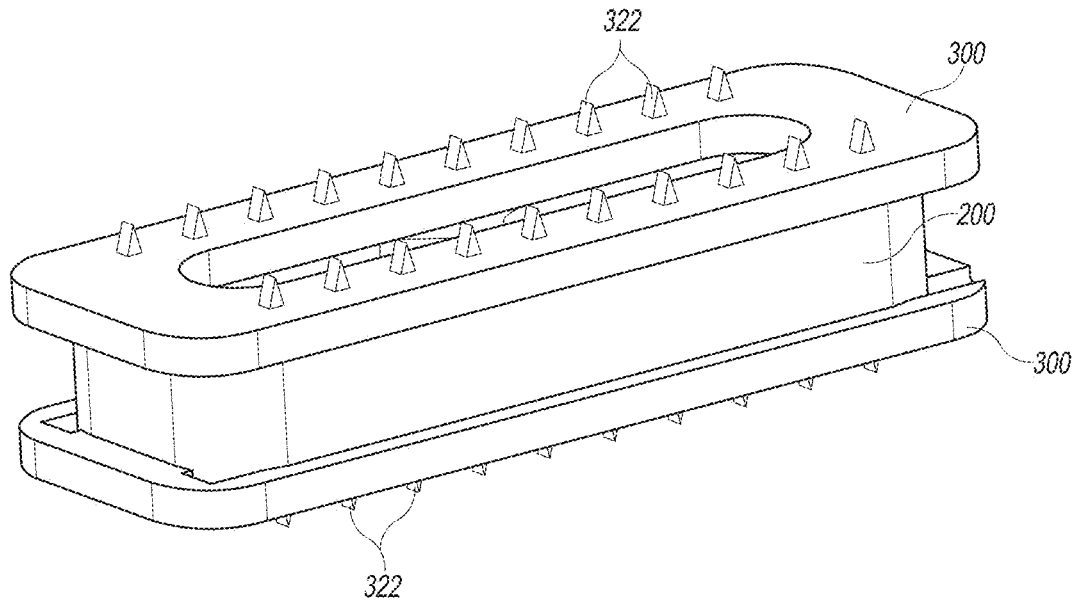
FIG. 12 illustrates a perspective view of one embodiment of an implant secured between upper and lower plates of a fusion system.

According to some embodiments, as illustrated in FIG. 11, the grooves or recesses 320 of the plates 300 can include one or more deployable teeth, spikes or other engagement features 322. For example, in one embodiment, the teeth or other features 322 are configured to be pushed through the bottom of the corresponding groove or recess 320, at least partially, when the protruding member or feature 220 of the implant 200 is moved over such teeth or features 322. Thus, the teeth, spikes or other engagement features 322 can be sequentially deployed away from the implant and toward the adjacent vertebral member. In some embodiments, the teeth or other engagement features 322 are deployed within the native tissue of the vertebral member to help secure the plates within the target intervertebral space during and after implantation. One schematic embodiment of an implant 200 that has passed within upper and lower plates 300 and has caused a number of teeth, spikes or other engagement features 322 to deploy away from the implant 200 is illustrated in FIG. 12.

Figure 13:
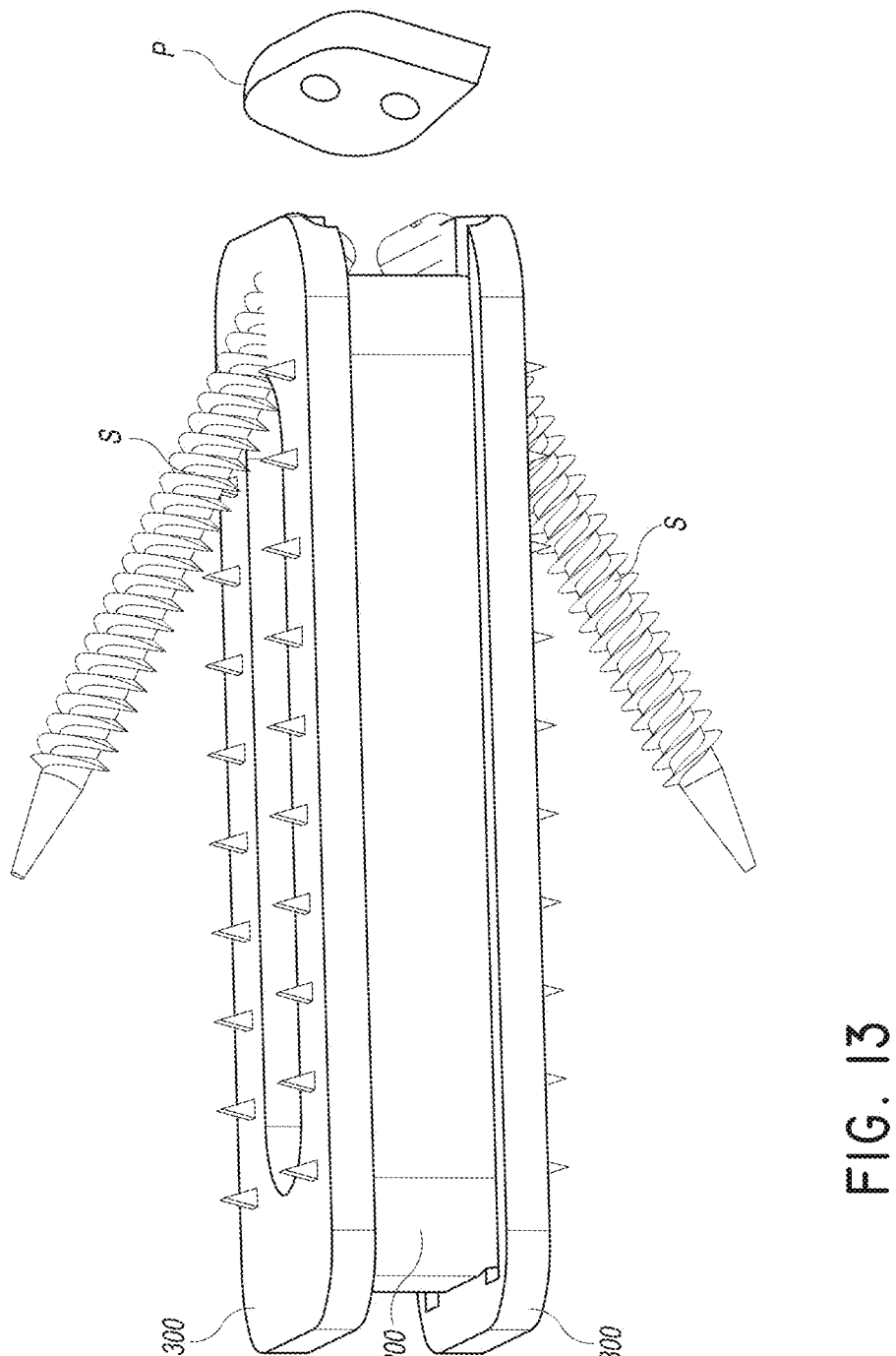
FIG. 13 illustrates a perspective view of one embodiment of an implant secured between upper and lower plates of a fusion system reinforced by two screws.
Figure 14:
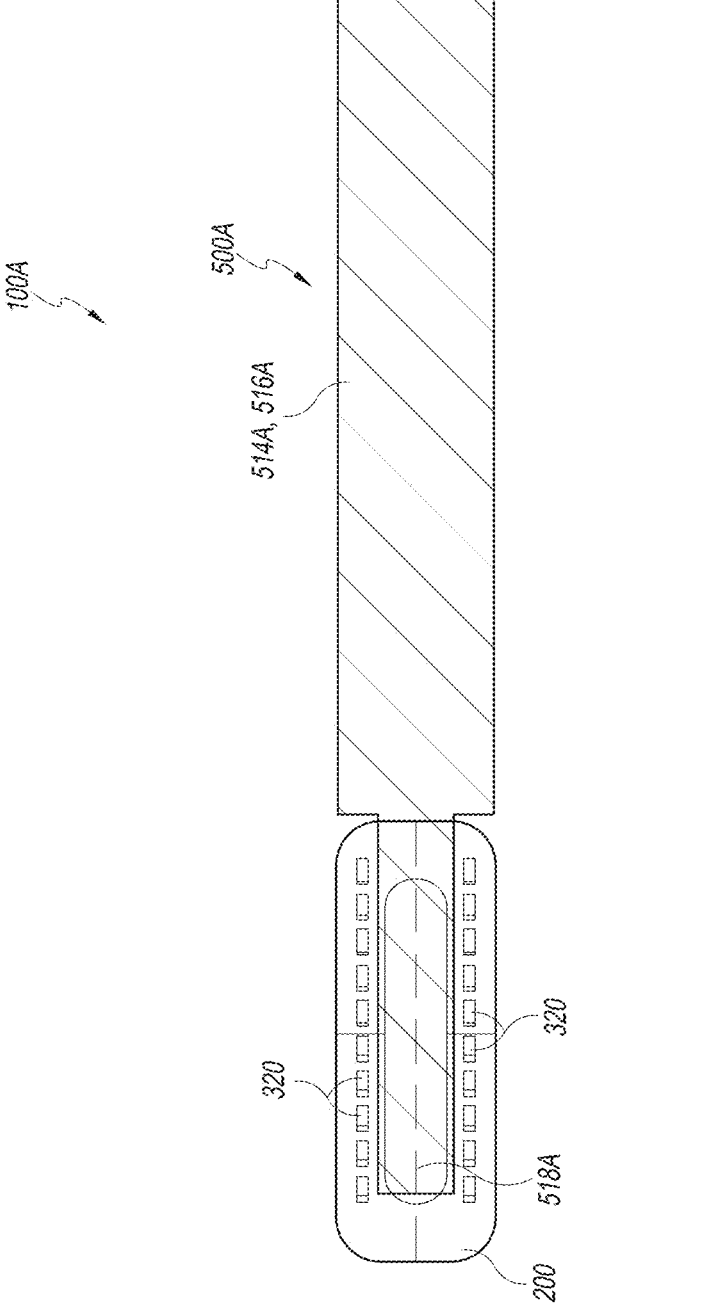
FIG. 14 illustrates a schematic top view of a portion of a guiding assembly and a corresponding plate configured for use with a spinal fusion system according to one embodiment.

As discussed in greater detail herein, after the implant 200 has been properly positioned between the plates 300 of the system, one or more screws or other fasteners can be used to further strengthen and reinforce the system. For example, as illustrated in FIG. 13, upper and lower screws S can be positioned through one or both of the plates 300 and/or the implant 200. Such screws can be advanced through one or more cortical structures of the adjacent vertebral members of the subject to provide additional strength and support to the fusion system. In some embodiments, one or more washers, plates or other rigid or semi-rigid members P can also be used in conjunction with the screws or other fasteners S. For example, the plate or other member P can include one or more holes or other openings that are sized, shaped, oriented and/or otherwise configured to secure a screw or other fastener therethrough, as desired or required. In some embodiments, the plate P is sized, shaped and configured to be flush or substantially flush with adjacent surfaces of the upper and lower vertebrae.

To assist in the description of the disclosed embodiments, words such as upward, upper, bottom, downward, lower, rear, front, vertical, horizontal, upstream, downstream have been used above to describe different embodiments and/or the accompanying figures. It will be appreciated, however, that the different embodiments, whether illustrated or not, can be located and oriented in a variety of desired positions.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

While the inventions are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods summarized above and set forth in further detail below describe certain actions taken by a practitioner; however, it should be understood that they can also include the instruction of those actions by another party. Thus, actions such as "advancing an implant" include "instructing advancing an implant." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 mm" includes "10 mm." Terms or phrases preceded by a term such as "substantially" include the recited term or phrase. For example, "substantially parallel" includes "parallel."

What is claimed is:

1. A method of inserting an implant within an intervertebral space defined between an upper vertebral member and a lower vertebral member, the method comprising:

positioning a plate system within the intervertebral space, wherein the plate system comprises an upper plate and a lower plate; and advancing an implant between the upper plate and the lower plate so that the implant is urged into the intervertebral space, the upper plate engages the upper vertebral member, and the lower plate engages the lower vertebral member;

wherein, upon advancement of the implant between the upper and lower plates, the upper vertebral member is distracted relative to the lower vertebral member;

wherein advancing the implant between the upper plate and the lower plate comprises advancing the implant at least partially through a guiding assembly; and wherein the guiding assembly comprises upper and lower guiding members or plates, wherein the upper and lower guiding members or plates are configured to removably engage corresponding portions of the upper and lower plates when the implant is advanced into the intervertebral space, wherein the upper and lower guiding members or plates establish a longitudinal passage for insertion of the implant.

2. The method of claim 1, wherein advancing an implant between the upper and lower base plates comprises using a device.

3. The method of claim 2, wherein the device comprises a mechanical device.

4. The method of claim 1, wherein advancing the implant between the upper plate and the lower plate comprises advancing the implant at least partially through a guiding assembly.

5. The method of claim 4, where the guiding assembly comprises upper and lower guiding members or plates, wherein the upper and lower guiding members or plates are configured to removably engage corresponding portions of the upper and lower plates when the implant is advanced into the intervertebral space.

6. A spinal fusion system comprising:

a plate system configured for placement within an intervertebral space of a subject, wherein the plate system comprises an upper plate and a lower plate;

an implant configured to be advanced and positioned between the upper plate and the lower plate to secure the implant within the intervertebral space;

wherein, when the implant is advanced between the upper plate and the lower plate, the upper plate engages the upper vertebral member, and the lower plate engages the lower vertebral member;

wherein, upon advancement of the implant between the upper and lower plates, the upper vertebral member is distracted relative to the lower vertebral member; and a guiding assembly comprising upper and lower slides, wherein the upper slide is configured to removably couple to the upper plate, and wherein the lower slide is configured to removably couple to the lower plate, wherein the upper and lower slides establish a longitudinal passage for insertion of the implant.

7. The system of claim 6, further comprising a rail system, and wherein the implant is configured to be advanced between the upper and lower plates using a rail system.

\* \* \* \* \*